US011453707B2

(12) United States Patent
Liu et al.

(10) Patent No.: US 11,453,707 B2
(45) Date of Patent: Sep. 27, 2022

(54) PROTEIN PRODUCT AND PREPARATION METHOD THEREOF

(71) Applicant: COFCO NUTRITION AND HEALTH RESEARCH INSTITUTE CO., LTD., Beijing (CN)

(72) Inventors: Zelong Liu, Beijing (CN); Benjun Sun, Beijing (CN); Xiaohui Xiong, Beijing (CN); Yu Wang, Beijing (CN); Jia Yang, Beijing (CN)

(73) Assignee: COFCO NUTRITION AND HEALTH RESEARCH INSTITUTE CO., LTD., Beijing (CN)

( * ) Notice: Subject to any disclaimer, the term of this patent is extended or adjusted under 35 U.S.C. 154(b) by 146 days.

(21) Appl. No.: 16/073,784

(22) PCT Filed: May 13, 2016

(86) PCT No.: PCT/CN2016/081942
§ 371 (c)(1),
(2) Date: Jul. 28, 2018

(87) PCT Pub. No.: WO2017/128556
PCT Pub. Date: Aug. 3, 2017

(65) Prior Publication Data
US 2019/0031728 A1    Jan. 31, 2019

(30) Foreign Application Priority Data

Jan. 28, 2016   (CN) .......................... 201610059449.4
Jan. 28, 2016   (CN) .......................... 201610059450.7
Jan. 28, 2016   (CN) .......................... 201610059633.9

(51) Int. Cl.
*C07K 14/425*      (2006.01)
*A23J 1/12*         (2006.01)
(Continued)

(52) U.S. Cl.
CPC ............. *C07K 14/425* (2013.01); *A23J 1/005* (2013.01); *A23J 1/006* (2013.01); *A23J 1/125* (2013.01); *A23J 3/346* (2013.01)

(58) Field of Classification Search
CPC ...... A23V 2250/5486; A23V 2250/548; A23V 2250/54252; A23V 2250/55;
(Continued)

(56) References Cited

U.S. PATENT DOCUMENTS 2,287,649 A    6/1942   Swallen
3,535,305 A    10/1970  Cater et al.
(Continued)

FOREIGN PATENT DOCUMENTS

CN    101107966 A    1/2008
CN    101390564 A    3/2009
(Continued)

OTHER PUBLICATIONS

Krishnan, H.B. and E.H. Coe Jr., Encyclopedia of Genetics, Seed Storage Proteins, 2001, Abstract. (Year: 2001).*
(Continued)

*Primary Examiner* — Hong T Yoo
(74) *Attorney, Agent, or Firm* — Volpe Koenig

(57) ABSTRACT

A protein product and an extraction method for making the protein product. Raw materials of the product optionally contains macromolecular carbohydrates and/or fat, and the method does not use organic solvents. The protein product contains prolamin and carbohydrates, wherein the prolamin accounts for 70 wt % or above of the protein (dry-basis), the $\alpha$-prolamin accounts for 75 wt % or above of the prolamin, the $\beta$-prolamin accounts for 20 wt % or below of the prolamin, and the $\gamma$-prolamin accounts for 6 wt % or below of the prolamin.

15 Claims, 7 Drawing Sheets

(51) Int. Cl.
*A23J 1/00* (2006.01)
*A23J 3/34* (2006.01)

(58) Field of Classification Search
CPC .. C07K 14/415; C07K 14/605; C07K 14/425; A23J 3/18; A23J 1/12; A23J 1/14; A23J 1/125; A23G 3/30; A23L 1/31
See application file for complete search history.

(56) References Cited

U.S. PATENT DOCUMENTS

| | | | |
|---|---|---|---|
| 5,968,585 A | | 10/1999 | Liaw et al. |
| 6,036,983 A | * | 3/2000 | Nielsen .................. A23J 3/341 426/20 |
| 6,602,985 B1 | | 7/2003 | McInnis et al. |
| 8,093,023 B1 | * | 1/2012 | Prevost .................... C12P 7/06 435/161 |
| 2007/0037267 A1 | * | 2/2007 | Lewis ...................... C12P 7/06 435/161 |
| 2008/0242842 A1 | | 10/2008 | Sessa |
| 2011/0097779 A1 | * | 4/2011 | Soong .................... C12P 7/065 435/161 |

FOREIGN PATENT DOCUMENTS

| | | |
|---|---|---|
| CN | 102532294 A | 7/2012 |
| CN | 103059116 A | 4/2013 |
| CN | 103160559 A | 9/2013 |
| CN | 103781796 A | 5/2014 |
| CN | 104041653 A | 9/2014 |
| JP | 2004059537 | 2/2004 |

OTHER PUBLICATIONS

Merriam Webster, definition wash, https://www.merriam-webster.com/dictionary/wash, retrived online Feb. 10, 2022 (Year: 2022).*

Timothy J. Anderson and Buddhi P. LamsaF3 "Zein Extraction from Corn, Corn Products, and Coproducts and Modifications for Various Applications" 2011, Cereal Chemistry, 88(2): 159-173.

John W. Lawton "Isolation of Zein Using 100% Ethanol" 2006, Cereal Chemistry Journal, 83(5): 565-568.

Timothy J. Anderson and Buddhi P. LamsaF3 "Development of New Method for Extraction of a-Zein from Corn Gluten Meal Using Different Solvents" 2011, Cereal Chemistry, 88(4): 356-362.

Gordon W. Selling and Kristen Kruger Woods "Improved Isolation of Zein from Corn Gluten Meal Using Acetic Acid and Isolate Characterization as Solvent" 2008, Cereal Chemistry, 85(2): 202-206.

H.D. Belitz W. Grosch and P. Schieberle "Food Chemistry" 4th revised and extended edition, 2009 © Springer-Verlag Berlin Heidelberg.

Panadda Nonthanum, Youngsoo Lee, and Graciela W. Padua "26-Joumal of Agricultural and Food Chemistry" Jan. 23, 2012, 60(7): 1742-1747—Published.

Selling G W, Woods K K. "Improved Isolation of Zein from Corn Gluten Meal Using Acetic Acid and Isolate Characterization as Solvent[J]" 2008, Cereal Chemistry, 85(2): 202-206.

Chen "Handbook of Corn Starch Industry" Sep. 2009, China Light Industry Press, pp. 134-141. English translation.

Pan Daodong "Functional Food Additives" Jan. 2006, China Light Industry Press, pp. 245-248. English translation.

Cui Yunhong "Technology and Management of Corn Starch Wet Milling" May 2007, Shandong Science and Technology Press, pp. 72-73. English translation.

Xu Yan-yan "Extraction and Characterization of Protein from Corn Yellow Flour" Apr. 15, 2013, Full-text Database of Excellent Masterchar(39)s Degree Thesis of China, Part I, No. 04, 2013, B024-151. (the closest prior art, which discloses a method of extracting protein from corn yellow flour) English translation.

Sen Yi et al. "New application of zein Grains and fats" 1993, (01):87 and translation for the cited OA. English translation.

Yunfeng Bi et al. "Progress in extraction of zein and biological activity of zein hydrolysate" 2015, The Food Industry, 36 (11):252-257. English translation.

Zhiguo Liu et al. "Preparation of ACE inhibitor from enzyme-degested zein" 2006, Food research and development, (02):138-141. English translation.

* cited by examiner

PROTEIN PRODUCT AND PREPARATION METHOD THEREOF

TECHNICAL FIELD

The present invention relates to a method for enriching α-prolamin from a raw material and a method for purifying a protein product, and also relates to a protein product obtained by the above method, belonging to the field of crop processing.

BACKGROUND

Zein is a product extracted from corn or corn-protein-containing substances, such as corn gluten meal, dried distillers' grains with solubles (DDGS), etc. Prolamin is the protein having the highest content in corn endosperm, accounting for 44 wt %-79 wt % of corn endosperm proteins. The corn gluten meal is mainly obtained from corn starch wet production. In the corn wet production, sulfurous acid is first prepared for soaking corn, the soaking water is separated from the corn and evaporated to obtain corn steep liquor, the corn is subjected to primary and secondary crushing to separate out the germ, the endosperm is subjected to fine grinding to separate out fibers, the starch milk is preconcentrated and subjected to a main separation step to separate out gluten, and the starch is washed, dewatered and dried to obtain the finished product. The gluten is concentrated, dewatered and dried to obtain the corn gluten meal; and the germ is dewatered, dried and subjected to corn oil extraction to obtain germ pulp, the fibers are dewatered and dried, and the corn steep liquor is sprayed on the dried fibers and germ pulp, respectively, to obtain the products, such as fibrous protein feed, high pulp feed, etc.

Zein is a pharmaceutical excipient in the Chinese Pharmacopoeia (2010) and is also approved by the US FDA. Zein is a generally recognized as safe (GRAS) substance that can be directly added to food. Corn protein has surface activity and unique film forming properties, can be used as a drug targeting loose carrier, a food preservation coating film, a biodegradable packaging material, chewing gum, protein fiber, etc., and is widely used in food, medicine, chemical and other fields.

Zein is an alcohol-soluble protein and is soluble in an aqueous solution of ethanol, isopropanol or acetone. It is insoluble in pure water or absolute ethanol. It mainly contains four components, namely α-prolamin (accounting for about 70 wt %-85 wt % of zein), β-prolamin (accounting for about 1 wt %-5 wt %), γ-prolamin (accounting for about 10 wt %-20 wt %), and δ-prolamin (accounting for about 1 wt %-5 wt %) (Cereal Chemistry, 2011, 88(2): 159-173). Among them, α-prolamin is the most important commercial zein. The technique for preparing zein mainly utilizes the difference in solubility of different prolamin components in the extraction solvent. In the corn gluten meal produced in the corn wet milling technique, the protein (dry-basis) content is about 65 wt %, and the corn gluten meal also mainly comprises about 15 wt %-20 wt % of starch, 10 wt %-13 wt % of fibers, and about 6 wt % of fat. Corn gluten meal is one of the main raw materials for commercial zein extraction. The commercial technique mainly uses the Swallen 1941 patent (U.S. Pat. No. 2,287,649A) and the Carter and Reck 1970 patent (U.S. Pat. No. 3,535,305), as shown in FIG. 3. Corn gluten meal is treated batchwise or continuously with isopropanol or 95% ethanol (v/v) at a higher pH and a temperature (50-60° C.). The extract is filtered or centrifuged, and excess cold water or low temperature is used (−10° C. to −25° C.) to precipitate prolamin. Vacuum drying and milling are performed to obtain the finished product. Of course, there are other or improved techniques for preparing zein, but all are process schemes using an organic solvent (U.S. Pat. No. 6,602,985B1; Cereal Chemistry Journal, 2006, 83(5): 565-568; Cereal Chemistry, 2011, 88(4): 356-362) or organic acid (Cereal Chemistry, 2008, 85(2): 202-206) as an extractant.

Researchers have also studied non-protein impurities in protein materials in order to remove them, thereby increasing the total protein content of the corn, or thereby enhancing the efficiency of subsequent solvent extraction. Cai Muyi et al., in the patent CN101390564, discloses the use of an alkali to heat-treat corn gluten meal to cause a portion of starch, fat, and pigment to become soluble and thus removed, thereby obtaining an isolated protein product mainly composed of prolamin and gluten. However, because there is starch attached to the fiber or protein in the corn gluten meal and the pigment (mainly zeaxanthin) is embedded in the inside of the protein, it is difficult to be removed by single gelatinization or saponification. The US CPC Corporation and Japan Showa Industry Co., Ltd. used freeze-decolorization to produce white zein (JP2004059537), but the technique involves the use of reagents with safety hazards such as methanol and acetone. Sessa discloses a method for decolorizing and deodorizing prolamin dissolved in an alcohol solution by using zeolite and activated carbon in the patent US20080242842. In addition, some people may use a solvent such as n-hexane or ethyl acetate to decolorize and deodorize the prolamin low-water-content raw material or the finished product. Further, the fat is removed by an enzyme such as a solvent or a lipase to further increase the total protein purity; and a chemical agent such as ozone, persulfuric acid or peroxide, or enzyme (such as lipoxygenase) is used for decolorization. However, a too high heating temperature can also cause amino acid residues from proteins to participate in the formation of certain harmful substances. For example, when the temperature is higher than 100° C., cysteine and methionine will react with glucose to form a toxic substance-acrylamide. (Food Chemistry, 4th revised and extended edition, edited by H. -D. Belitz, W. Grosch and P. Schieberle, Pages 25-29). Liaw et al. (U.S. Pat. No. 5,968,585A) utilizes a membrane separation technique to separate starch from protein in the endosperm to obtain liquor having a protein (dry-basis) content of about 70 wt %. At present, various extraction techniques of organic solvents or organic solvent aqueous solutions for preparing zein still have problems of solvent loss, high use cost, difficulty in treating solvent wastewater and high energy consumption during large temperature rise and fall operations, which need to be further solved. In addition, gelation that occurs during the extraction technique is another drawback of the organic solvent or organic solvent aqueous extraction and separation process, mainly due to the presence of γ-prolamin (Journal of Agricultural and Food Chemistry 60(7): 1742-1747). There is a technique to adjust the pH to 11.5 and keep the temperature at 70° C. for 30 minutes to prevent gelation. However, the protein will undergo partial peptide bond hydrolysis in the strong base environment and deamidation of asparagine and glutamine or sulfhydryl destruction. In addition, the acid adjustment step in the later stage will also cause the system to produce more salt. It has also been studied to extract prolamin by using a 90% acetic acid-water solution (v/v), but the fat content is higher than that of the alcohol extract protein product, and the tensile strength as a material is also low (Selling G W, Woods K K. Improved Isolation of Zein from Corn Gluten Meal Using Acetic Acid and Isolate Characterization as Solvent[J]. Cereal Chemistry, 2008, 85(2): 202-206). There are also techniques for modifying alcohol-extracted prolamin into a product for aqueous applications by chemical treatment (CN103781796A). However, there is currently no technique for producing prolamin in an aqueous system that is completely free of organic solvents (such as ethanol, isopropanol, etc.) or high levels of organic acids (such as 90% acetic acid).

SUMMARY

Finding a new production technique for prolamin while more effectively utilizing other component resources in related raw materials becomes a problem faced by those skilled in the art, but is also most likely an effective way to reduce production cost. Therefore, it would be very beneficial to provide a prolamin product separated from a raw material containing an alcohol-soluble protein under a mild pH (pH=3-11) without an organic solvent. It would also be very beneficial to provide a method for producing the product. It would also be very beneficial to provide a system for implementing the method.

The inventor first discovers through research on various components in the corn protein raw material including different protein components: for different components, especially protein components, the corresponding enzymes and separation methods can be used, the effect of purifying zein, especially α-prolamin, can be achieved in an aqueous environment that does not contain an organic solvent (with a mild pH, pH=3-11), and the content of β-/γ-prolamin in the product can be controlled; and meanwhile, a variety of useful byproducts are formed, thereby giving starch or ethanol producers a good opportunity for the deep development and utilization of corn protein.

A first aspect of the present invention relates to a method for enriching α-prolamin from a raw material, the raw material comprising prolamins and non-prolamin and optionally comprising macromolecular carbohydrates (the macromolecular carbohydrates in the invention mainly include starch and cellulose) and/or fat, characterized in that the method does not use organic solvents and comprises the following steps:

(1) milling and slurrying the raw material;
(2) using protease treatment to completely hydrolyze or partially hydrolyze at least a part of β-prolamin, γ-prolamin and non-prolamin in the raw material, and performing filtration by using the difference in particle size to remove the hydrolysate, thereby obtaining a crude product in which α-prolamin is enriched; and
(3) washing, dewatering and drying the crude product to obtain a final product.

A second aspect of the present invention relates to a method for purifying a protein product from a raw material, the raw material comprising β-prolamin, γ-prolamin and non-prolamin and optionally comprising macromolecular carbohydrates and/or fat, characterized in that the method does not use organic solvents and comprises the following steps:

(1) milling and slurrying the raw material;
(2) using hydrolase treatment to completely hydrolyze or partially hydrolyze at least a part of macromolecular carbohydrates in the raw material, and performing filtration by using the difference in particle size to remove the hydrolysate, thereby obtaining a protein crude product; and
(3) washing, dewatering and drying the protein crude product to obtain a final protein product.

A third aspect of the present invention relates to a protein product obtained according to the above-mentioned aspects of the present invention, the protein product comprising prolamins and carbohydrates, characterized in that the prolamin accounts for 70 wt % or above of the protein (dry-basis); and in the meanwhile, the α-prolamin accounts for 75 wt % or above of the prolamin, the β-prolamin accounts for 20 wt % or below of the prolamin, and the γ-prolamin accounts for 6 wt % or below of the prolamin.

In a preferred embodiment of the above-mentioned aspects of the present invention, the raw material is selected from the group consisting of corn gluten meal, corn endosperm fermented mash and distiller's grains.

In a preferred embodiment of the above-mentioned aspects of the present invention, the protease is one or more selected from the group consisting of carboxyl protease, serine protease, metalloprotease and thiol protease. Preferably, the carboxyl protease is a mold carboxyl protease, preferably an *Aspergillus* carboxyl protease, more preferably an *Aspergillus oryzae* carboxyl endoprotease; the serine protease is a *Bacillus* serine protease, preferably a *Bacillus subtilis* serine endoprotease; the metalloprotease is a mold or *Bacillus* metalloprotease, preferably an *Aspergillus oryzae* metalloendoprotease or *Bacillus subtilis* metalloendoprotease; and the thiol protease is a plant-derived thiol protease, preferably bromelain and/or papain.

In a preferred embodiment of the above-mentioned aspects of the present invention, the hydrolase is one or more selected from the group consisting of α-amylase, saccharifying enzyme, cellulase, β-glucanase, pullulanase, xylanase, pectinase, arabanase and hemicellulase. Preferably, the α-amylase is a mold or bacterial a-amylase, preferably a mold α-amylase, more preferably an *Aspergillus* α-amylase; the saccharifying enzyme is a mold glucoamylase, preferably an *Aspergillus* or *Trichoderma* glucoamylase; the cellulase is a mold cellulase, preferably a *Trichoderma* cellulase; the β-glucanase is a fungal or bacterial β-glucanase; and the pullulanase is a *Bacillus* pullulanase.

In a preferred embodiment of the above-mentioned aspects of the present invention, during the protease treatment or hydrolase treatment, a reagent composition is optionally added to adjust the enzyme, and the reagent composition is one or more selected from the group consisting of the following substances: a compound capable of breaking a disulfide bond in a protein, such as a phosphorus-containing compound or a sulfur-containing compound, wherein the phosphorus-containing compound is preferably tris(2-carboxyethyl)phosphine, and the sulfur-containing compound is preferably a compound containing a free thiol group and/or a compound capable of providing a sulfite group, more preferably mercaptoethanol, dithiothreitol, cysteine and oligopeptide comprising cysteine (peptide consisting of 2-10 amino acids), sulfite, sulfurous acid, bisulfite and pyrosulfite; metal ion, preferably alkali metal ion, alkaline earth metal ion and divalent transition metal ion, more preferably sodium ion, potassium ion, magnesium ion, calcium ion, manganese ion, cobalt ion and zinc ion; and a metal chelator, preferably EDTA and EGTA.

In a preferred embodiment of the above-mentioned aspects of the present invention, the protease treatment is performed under the following conditions: pH 3.5-10.5, preferably 3.8-10; treatment temperature 20° C.-65° C., preferably 35° C.-55° C.; treatment time 0.2 h-10 h, preferably 0.5 h-5 h. More preferably, the conditions are selected from: pH 4.8, 45° C.; pH 7.5, 52° C.; pH 3.8, 35° C.; pH 8.3, 52° C.; pH 8.5, 65° C.; pH 6.5, 45° C.; pH 8.0, 45° C.; pH 10.2, 45° C.; pH 4.2, 35° C.; pH 6.5, 45° C.; pH 4.8, 55° C.; pH 4.8, 53° C.; pH 7.2, 53° C.; pH 7.5, 25° C.; and pH 10.1, 55° C.

In a preferred embodiment of the above-mentioned aspects of the present invention, the hydrolase treatment is performed under the following conditions: pH 3-8, preferably 3.3-7.5, more preferably 4-6.5, most preferably 4.5-5.5; treatment temperature 30° C.-72° C., preferably 35° C.-63° C., more preferably 40° C.-60° C., most preferably 45° C.-55° C.; treatment time 0.5 h-12 h, preferably 1 h-10 h, more preferably 2 h-8 h, most preferably 2 h-7 h; and more preferably, the hydrolase treatment conditions are selected from: pH 5.0, 63° C.; pH 5.5, 50° C.; pH 3.0, 35° C.; pH 6.5, 45° C.; pH 4.0, 40° C.; pH 6.5, 45° C.; pH 4.5, 60° C.; pH 8, 45° C.; pH 5, 55° C.; pH 7.5, 50° C.; pH 3.5, 30° C.; pH 5.6, 50° C.

In a preferred embodiment of the above-mentioned aspects of the present invention, the filtration is performed by using a filtration pore size of 1 μm-80 μm, preferably 10 μm-50 μm, or a membrane filtration pore size of 10 nm-10 μm, preferably 20 nm-1 μm.

In a preferred embodiment of the above-mentioned aspects of the present invention, the prolamin accounts for 74 wt % or above of the protein (dry-basis), preferably 80 wt % or above, more preferably 85 wt % or above, further preferably 90 wt % or above, further more preferably 95 wt % or above, most preferably 97 wt % or above; the α-prolamin accounts for 77 wt % or above of the prolamin, preferably 85 wt % or above, more preferably 90 wt % or above, further preferably 95 wt % or above, most preferably 100 wt %; the β-prolamin accounts for 10 wt % or below of the prolamin, preferably 5 wt % or below, more preferably 3 wt % or below, further preferably 2 wt % or below, most preferably 0%; the γ-prolamin accounts for 10 wt % or below of the prolamin, preferably 5 wt % or below, more preferably 2 wt % or below, most preferably 0%; and the protein (dry-basis) accounts for 85 wt % or above of the protein product, preferably 90 wt % or above, more preferably 94 wt % or above, most preferably 99 wt % or above.

Compared with the method for preparing prolamin in the prior art, the technical solution involved in the present application has the following advantages:

The total protein content and the contents of α-prolamin, β-prolamin and γ-prolamin in the prolamin product of the present invention are not significantly different from those of the product obtained by the conventional extraction method using other organic solvents such as ethanol and isopropanol. Alpha-prolamin is the most important protein component that provides functionality such as film forming properties. The content of α-prolamin in the prolamin product of the present invention in the total protein may be higher than that of the product prepared by the conventional technique.

Under the condition of without performing a separate decolorization technique, the prolamin product of the present invention has lighter color than the yellow prolamin product prepared by the conventional method, is close to white in color, and also has a lower characteristic odor of corn than the product prepared by the traditional method; and the product has a wider application range and can be used in food in large amount without affecting the appearance and flavor of the original food.

The prolamin product of the present invention is not significantly different from the product obtained according to the traditional extraction method using ethanol, isopropanol and other organic solvents in the aspects of solubility in an alcohol solution, film forming properties, fiber forming properties, formability, microsphere preparation characteristic, degradability and other functional characteristics, and for some characteristics, such as microsphere water solution stability and the like, the prolamin product of the present invention is even superior to the product prepared by the traditional technique.

The preparation method of the prolamin product according to the present invention can specifically retain α-prolamin in one step while freely adjusting the content of β-prolamin and γ-prolamin in the product, and does not need to separate the α-prolamin, β-prolamin and γ-prolamin step by step by using the organic solvent water solution and adjusting the concentration of the organic solvent according to the traditional preparation method.

Since the preparation method of the prolamin product according to the present invention is performed in a full aqueous phase system, the material gelation in the preparation process can be completely avoided even if the γ-prolamin is retained, thereby producing the product with the γ-prolamin and thus greatly expanding the type of the prolamin product.

The preparation method of the prolamin product according to the present invention can implement separation of starch and derivatives thereof from the prolamin under the condition of low degradation of starch (DE value <40) or a starch non-gelatinization state.

While the preparation method of the prolamin product according to the present invention can produce the prolamin product, the refined raw materials of the crude sugar product or the oligosaccharide, disaccharide and monosaccharide products, and other feed-grade or food-grade protein byproducts can be coproduced.

Compared with the traditional preparation method, the preparation method of the prolamin product according to the present invention can obtain the bright-color creamy white prolamin product with weak original characteristic odor without any special decolorization or deodorization technique.

In the process involved in the preparation method of the prolamin product according to the present invention, since only the water is used as the medium in the whole process and the ethanol, acetone, n-hexane, ethyl acetate and other solvents belonging to fire hazard class A used in the conventional extraction technique are not used, the workshop has a low explosion-proof grade and the production process is safe.

The equipment involved in the preparation method of the prolamin product according to the present invention is conventional equipment for the chemical process and food and drug processing, so the equipment input cost is lower. Moreover, the raw materials used can be prepared without dewatering or drying, and so partial energy consumption can be lowered.

DETAILED DESCRIPTION

The corn protein and a preparation method thereof provided by the present invention will be further described in detail below with reference to the accompanying drawings.

Figure 1:
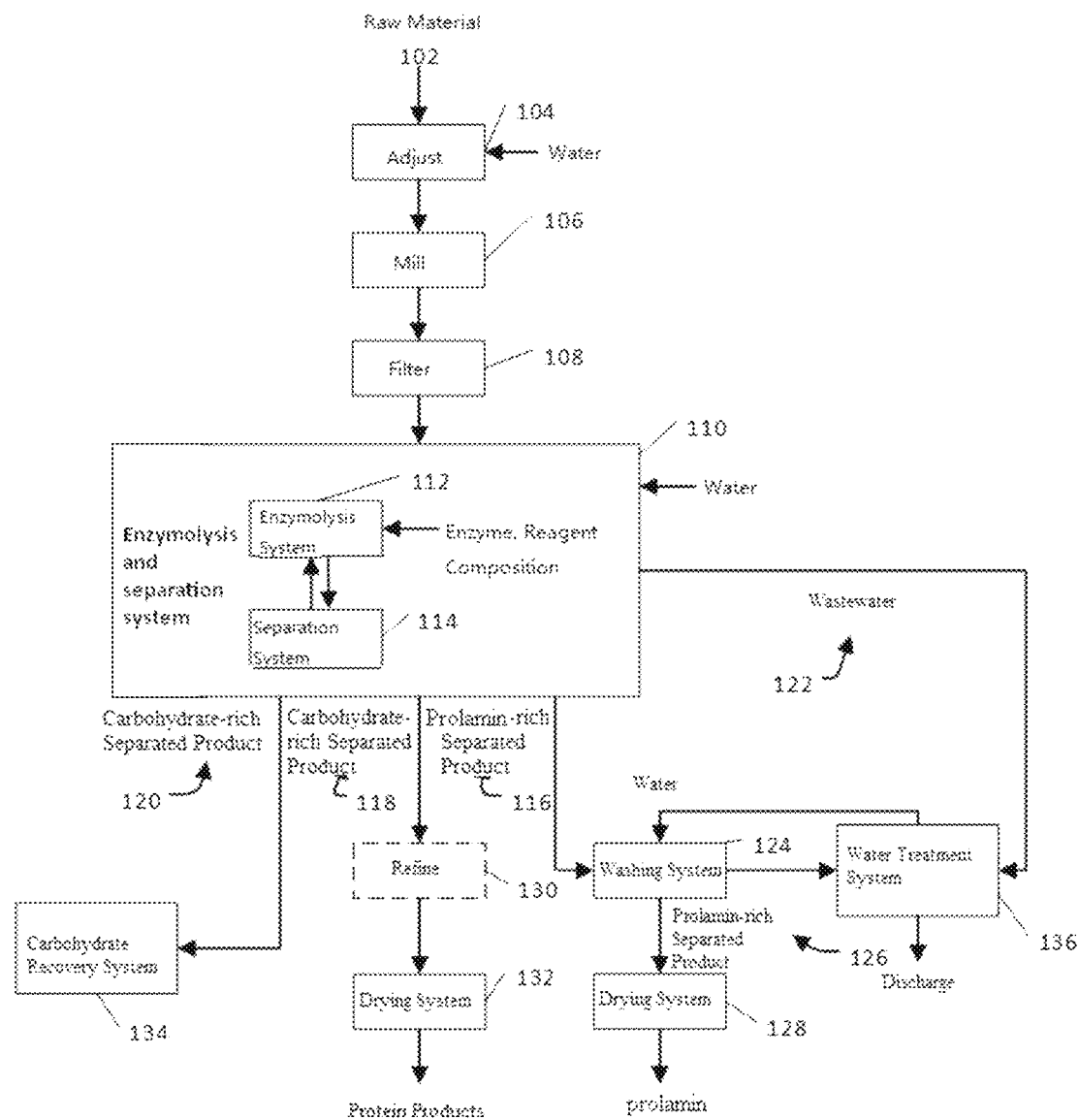
FIG. 1 is a process flow diagram of the prolamin production technique according to the present invention.

FIG. 1 is a process flow diagram of a technique for extracting prolamin from a zein raw material. After the raw material 102 is adjusted 104 with water and milled 106, material granules with suitable size are obtained by 108, and the slurry containing the material granules enters an enzymatic separation system 110 composed of an enzymatic system 112 and a separation system 114 by series connection, parallel connection or series-parallel connection; and in 110, parts of the material, such as starch, fibers and other carbohydrates, are degraded and non-prolamin components are degraded or/and modified, and the components are separated. A prolamin-rich separated product 116 obtained by 110 enters a washing system 124, and the obtained prolamin-rich separated product 126 is dried 128 to obtain a prolamin product. A protein-rich separated product 118 may also be obtained by 110, and enters a drying system 132 or is refined 130 and enters a drying system 132 to obtain a protein product. A carbohydrate-rich separated product 120 may also be obtained by 110, and can enter a carbohydrate recovery system 132 for utilization. Wastewater produced by the enzymatic separation system 110 and washing water produced by the washing system enter a water treatment system 136.

The equipment used in the implementation process of the zein production technique is exemplarily illustrated in FIG. 2. The basically identical equipment is used for different raw materials (such as corn gluten meal, corn endosperm fermented mash and dried distiller's grains) and target substances (prolamin including β- and γ-prolamin and rich in α-prolamin, prolamin including β-prolamin and rich in α-prolamin, and α-prolamin). According to an exemplary implementation, the raw material used is corn gluten meal slurry. According to another implementation, the raw material used is corn endosperm fermented mash dry powder.

Figure 2A:
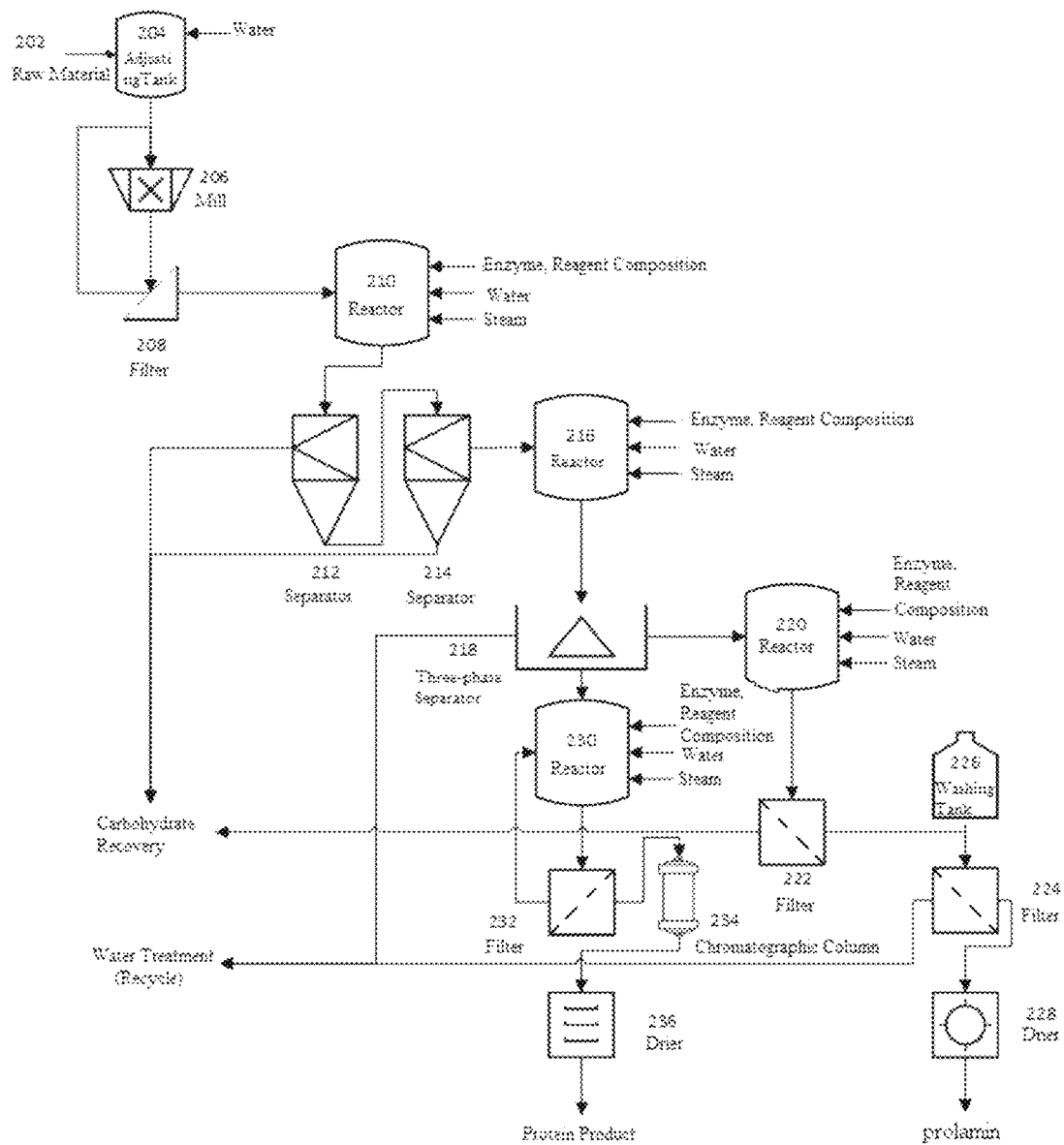
FIGS. 2A and 2B are production equipment diagrams for implementing the prolamin production technique according to the present invention.

FIG. 2A is a process flow diagram of a technique for extracting prolamin from corn gluten meal slurry. According to an exemplary implementation, the corn gluten meal slurry 202 is added with water and mixed in an adjusting tank 204 and enters a mill 206, such as a colloid mill.

According to an exemplary implementation, the water content of the material in 204 is adjusted to 95%; and according to a preferred implementation, the water content is adjusted to 75%-90%.

As illustrated, the liquid passes through a filter 208 and enters a first enzymatic reactor 210 together with an enzyme (such as composite cellulase), a reagent composition (such as sodium hydroxide, sodium metabisulfite), water, steam and the like. The mixture sequentially enters first separators 212 and 214, such as cyclone separators, the obtained prolamin material enters a second enzymatic reactor 216 together with an enzyme (such as protease), a reagent composition (such as sodium hydroxide, divalent manganese ion and disodium edetate (EDTA-2Na)), water, steam and the like to react, and the product enters a centrifuge 218, such as a three-phase disk centrifuge.

According to an exemplary implementation, the material in 216 is adjusted to a pH of 7.5 by using sodium hydroxide, a Bacillus subtilis neutral protease accounting for 0.3% by weight of protein, a Bacillus subtilis alkaline protease accounting for 0.5% and 0.1 mM $Mn^{2-}$ are added and held at 55° C. for 1.5 hours, and 0.05 mM EDTA-2Na is added.

As illustrated, the prolamin material obtained by the centrifuge 218 enters a third enzymatic reactor 220 together with an enzyme (such as amylase), a reagent composition (such as hydrochloric acid), water, steam and the like. After the reaction is finished, the product sequentially enters filter units 222 and 224, is washed in 224, and enters a drier 228 to obtain a prolamin finished product.

According to an exemplary implementation, devices 222 (which may be, for example, a microfiltration membrane device) and 224 (which may be, for example, a plate and frame filter press) may implement a final separation of the non-prolamin component and the prolamin.

As illustrated, the non-prolamin protein component obtained by the centrifuge 218 may enter an enzymatic reactor 230 together with an enzyme (such as protease), a reagent composition (such as hydrochloric acid), water, steam and the like for further treatment, is subjected to selective permeation and concentrated through a filter bank 232 (such as a 100 nm-20 nm ultrafiltration membrane bank), and is refined through a chromatographic column 234 (such as an ion exchange column) and dried to obtain a protein product. Carbohydrate-containing liquids of 212 and 214 may be recovered; and a third phase liquid of 218 and washing water of 224 may enter a water treatment system.

Figure 2B:
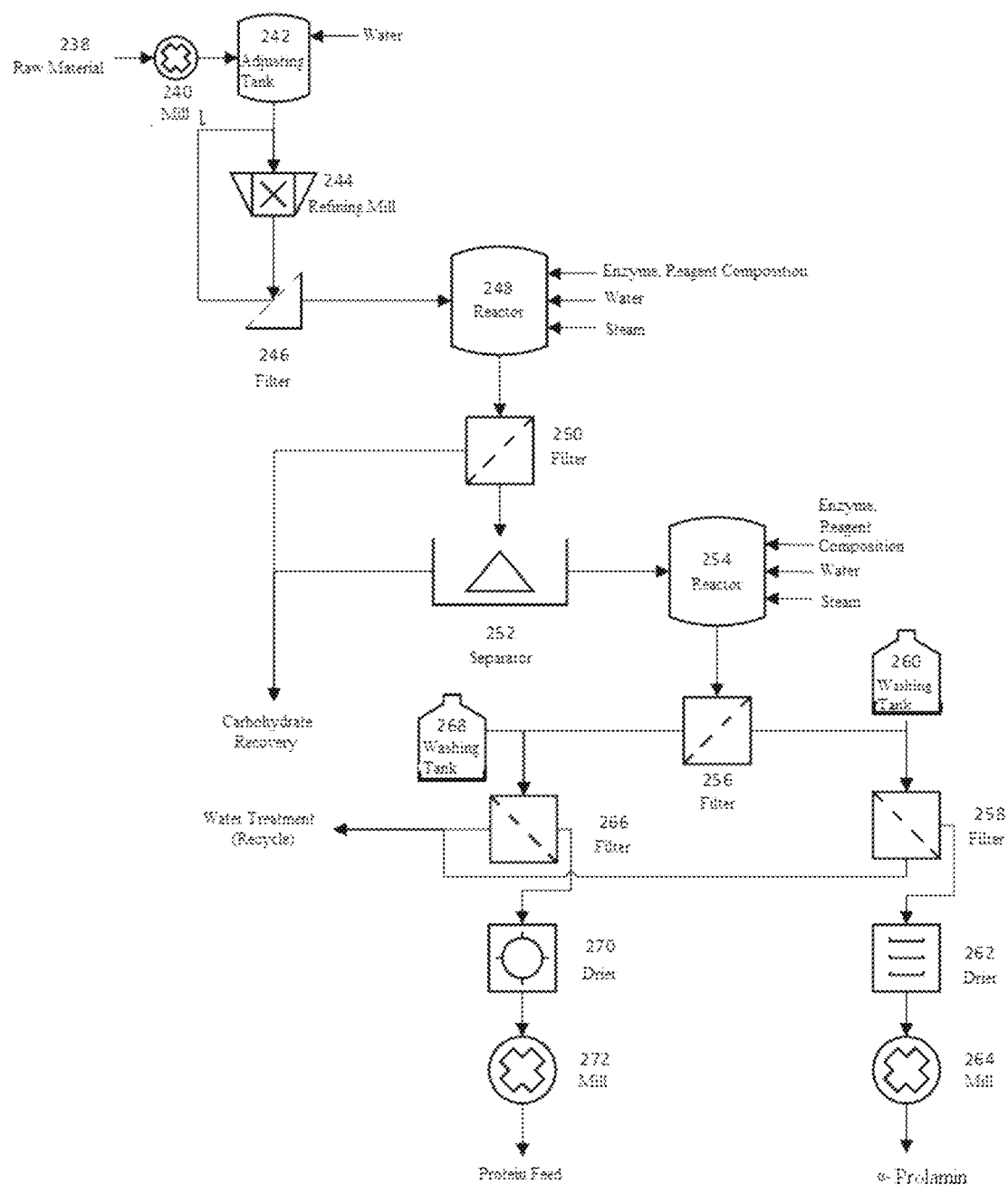
Figure 3:
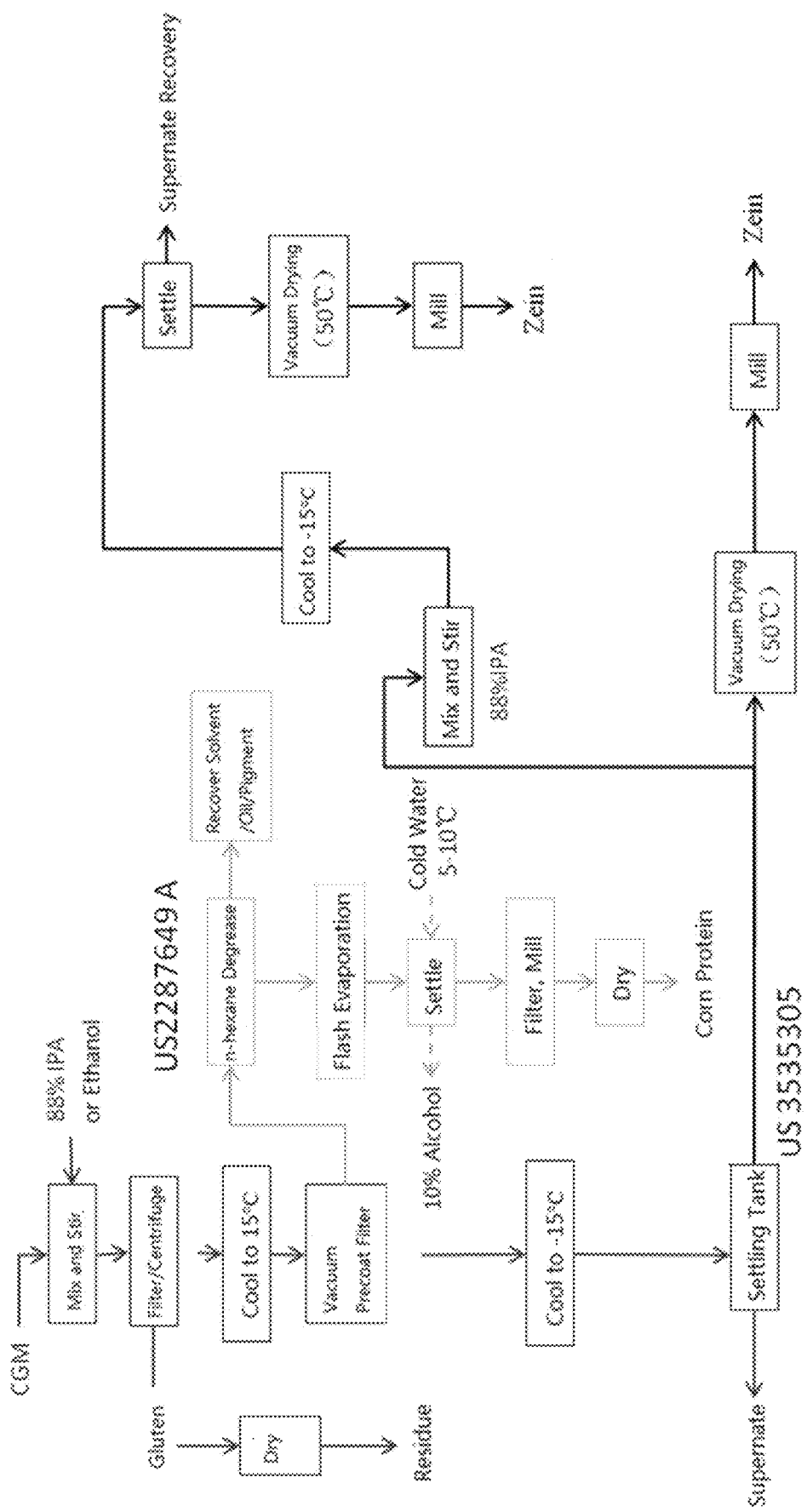
FIG. 3 is a main processing technique of zein in the prior art.

FIG. 2B is a process flow diagram of a technique for extracting high-purity α-prolamin from corn endosperm fermented mash dry powder. According to an exemplary implementation, the corn gluten meal is milled by a mill 240 (such as a roller press), enters an adjusting tank 242, is mixed with water and driven into a refining mill 244, passes through a filter 246, and enters a reactor 248.

According to an exemplary implementation, the filter 246 may have a filter pore size of, for example, 200 mesh.

As illustrated, the liquid enters the first reactor 248 together with an enzyme (such as composite cellulase/amylase), a reagent composition (such as potassium hydroxide), water, steam and the like, and after the reaction is finished, the mixture is driven into a filter 250.

According to an exemplary implementation, the filter 250 may have a filter pore size of, for example, 300 mesh.

As illustrated, the material passing through 250 enters a separating machine 252 (such as a decanter centrifuge) for separation, and the obtained prolamin-containing heavy phase material enters a second enzymatic reactor 254 together with an enzyme (such as protease), a reagent composition (such as sodium hydroxide and divalent calcium ion), water, steam and the like for reaction. The retentate of the filter 250 and the clear liquid of the separating machine 252 can be subjected to carbohydrate recovery.

According to an exemplary implementation, 254 may also be two enzymatic reactor sets (254-1 and 254-2) connected in series; and in the 254-1 reactor, the material is adjusted to pH 4.2 with hydrochloric acid, added with fungal acid neutral protease accounting for 0.8% by weight of protein and tris(2-carboxyethyl)phosphine accounting for 1% by weight of protein, and held at 45° C. for 2 hours. The product enters the 254-1 reactor, is adjusted to pH 8.3 with potassium hydroxide and added with *Bacillus subtilis* alkaline protease accounting for 0.3% by weight of protein and 0.1 mM $Ca^{2+}$, and reacts at 50° C. for 0.5 hour.

As illustrated, the material from 254 enters the filter 256 for separation, the retentate enters a filter 258, is washed with water (260), enters a drier 262 (such as a freeze drier), and is milled by a mill 264 to obtain a high-purity α-prolamin product. The permeated material in the filter 256 enters the filter 266, the retentate is washed (268) and enters a drier 270 (such as a pipe bundle drier) for drying, and is milled by a mill 272 (such as a hammer mill) to obtain a protein feed product. Permeated liquids of the filters 258 and 266 are discharged into a water treatment system.

According to an exemplary implementation, the filter 258 may have a filter pore size of, for example, 500 mesh.

The working parameters of zein extraction are set forth in Table 1 below, which provide a typical range and a preferred range for each of operation steps. The typical range of the milled particle size of the raw material is 2-150 μm. The preferred range of the milled particle size of the raw material is 10-100 μm (the particle size and the number of meshes can be converted with reference to the table). The typical range for water content adjustment of the raw material is 50%-95%. The preferred range for water content adjustment of the raw material is 75%-90%. The typical range of the addition amount of the protease is 0.01 wt %-10 wt % based on the weight of the protein in the raw material. The preferred range of the addition amount of the protease is 0.1 wt %-3 wt % based on the weight of the protein in the raw material. The typical range of protease enzymolysis pH is 3.5-10.5. The preferred range of protease enzymolysis pH is 3.8-10. The typical range of protease enzymolysis temperature is 20° C.-65° C. The preferred range of protease enzymolysis temperature is 35° C.-55° C. The typical range of protease enzymolysis time is 0.2 h-10 h. The preferred range of protease enzymolysis time is 0.5 h-5 h. The typical range of the addition amount of the amylase is 0.05 wt %-20 wt % based on the weight of the starch in the raw material. The preferred range of the addition amount of the amylase is 0.25 wt %-15 wt % based on the weight of the starch in the raw material. The typical range of amylase enzymolysis pH is 3-8. The preferred range of amylase enzymolysis pH is 3.3-7.5. The typical range of amylase enzymolysis temperature is 30° C.-72° C. The preferred range of amylase enzymolysis temperature is 35° C.-63° C. The typical range of amylase enzymolysis time is 1 h-10 h. The preferred range of amylase enzymolysis time is 2 h-7 h. The typical range of the addition amount of the cellulase enzymolysis is 0.2 wt %-30 wt % based on the weight of the fiber in the raw material. The preferred range of the addition amount of the cellulase enzymolysis is 0.5 wt %-20 wt % based on the weight of the fiber in the raw material. The typical range of cellulase enzymolysis pH is 4-6.5. The preferred range of cellulase enzymolysis pH is 4.5-5.5. The typical range of cellulase enzymolysis temperature is 40° C.-60° C. The preferred range of cellulase enzymolysis temperature is 45° C.-55° C. The typical range of cellulase enzymolysis time is 0.5 h-12 h. The preferred range of cellulase enzymolysis time is 2 h-8 h. The alkali comprises sodium hydroxide and potassium hydroxide. The addition amount of the alkali is determined according to the reaction pH. The acid comprises hydrochloric acid, sulfuric acid, sulfurous acid and organic acids (including lactic acid, citric acid and malic acid). The addition amount of the acid is determined according to the reaction pH. The addition condition of the reagent composition in the system to the liquid (the concentration is the molar concentration of the aqueous portion of the liquid): the typical range of the addition amount of the sulfur-containing compound is 1 mM-50 mM. The preferred range of the addition amount of the sulfur-containing compound is 5 mM-30 mM. The typical range of the addition amount of the phosphorus-containing compound is 0.5 mM-60 mM. The preferred range of the addition amount of the phosphorus-containing compound is 2 mM-40 mM. The typical range of the addition amount of the sodium ion, potassium ion, divalent alkaline earth metal ion and divalent transition metal ion is 0.01 mM-20 mM. The preferred range of the addition amount of the sodium ion, potassium ion, divalent alkaline earth metal ion and divalent transition metal ion is 0.1 mM-12 mM. The typical range of the addition amount of the metal chelator is 0 mM-35 mM. The preferred range of the addition amount of the metal chelator is 0.1 mM-18 mM. The typical range of the working pressure in the reaction vessel is −0.1 MPa to 0.3 MPa. The typical range of centrifugal force is 200 g-150000 g. The preferred range of centrifugal force is 1000 g-7000 g. The typical range of the filter pore size is 1 μm-80 μm. The preferred range of the filter pore size is 10 μm-50 μm. The typical range of the membrane filter pore size is 10 nm-10 μm. The preferred range of the membrane filter pore size is 20 nm-1 μm.

In the hydrolysis system of the present invention, an acid or an alkali acts as a pH adjuster, and is used for adjusting the reaction in a suitable acid-base environment and also used for adjusting the dissolved state of the components. The sulfur-containing compound, phosphorus-containing compound and metal ion are mainly used for adjusting the structure of the protein substrate, in particular, for breaking a disulfide bond in the protein substrate, so theoretically, any suitable compound capable of opening the disulfide bond in the protein may be selected. The metal ion and chelator are used for adjusting the activity or stability of the protease, carbohydrase and other enzymes.

TABLE 1

| Working parameters for extracting prolamin | | | |
|---|---|---|---|
| | | Typical Range | Preferred Range |
| Milled Particle Size μm | | 2-150 | 10-100 |
| Water Content Adjustment % | | 50 wt %-95 wt % | 75 wt %-90 wt % |
| Proteolysis | Addition Amount of Enzyme (in Protein by Weight) | 0.01 wt %-10 wt % | 0.05 wt %-3 wt % |
| | pH | 3.5-10.5 | 3.8-10 |
| | Temperature | 20° C. -65° C. | 35° C. -55° C. |
| | Time | 0.2 h-10 h | 0.5 h-5 h |

TABLE 1-continued

Working parameters for extracting prolamin

| | | Typical Range | Preferred Range |
|---|---|---|---|
| Amylolysis | Addition Amount of Enzyme (in Starch by Weight) | 0.05 wt %-20 wt % | 0.25 wt %-15 wt % |
| | pH | 3-8 | 3.3-7.5 |
| | Temperature | 30° C. -72° C. | 35° C. -63° C. |
| | Time | 1 h-10 h | 2 h-7 h |
| Fiber Hydrolysis | Addition Amount of Enzyme (in Fiber by Weight) | 0.2 wt %-30 wt % | 0.5 wt %-20 wt % |
| | pH | 4-6.5 | 4.5-5.5 |
| | Temperature | 40° C. -60° C. | 45° C. -55° C. |
| | Time | 0.5 h-12 h | 2 h-8 h |
| pH Adjuster | Alkali | Comprising sodium hydroxide and potassium hydroxide. The addition amount of alkali is determined according to the reaction pH. | |
| | Acid | Comprising hydrochloric acid, sulfuric acid, sulfurous acid and organic acids (including lactic acid, citric acid and malic acid). The addition amount of acid is determined according to the reaction pH. | |
| Reagent Composition | Sulfur-containing Compound | 1 mM-50 mM | 5 mM-30 mM |
| | Phosphorus-containing Compound | 0.5 mM-60 mM | 2 mM-40 mM |
| | Sodium Ion, Potassium Ion, Divalent Alkaline Earth Metal Ion and Divalent Transition Metal Ion | 0.01 mM-20 mM | 0.1 mM-12 mM |
| | Metal Chelator | 0 mM-35 mM | 0.1 mM-18 mM |
| Separation | Centrifugal Force | 200 g-150000 g | 1000 g-7000 g |
| | Filter Pore Size | 1 μm-80 μm | 10 μm-50 μm |
| | Membrane Filter Pore Size | 10 nm-10 μm | 20 nm-1 μm |

It should be noted that the values of the composition of the extraction raw materials and the composition of the protein finished product as described in the following examples are not used to limit the extraction raw material and protein finished product to the specific products, but are merely used to describe the objective parameters of the extraction raw materials or protein finished product.

In the present invention, the protein content in the product is determined according to the "first method" in "National Food Safety Standard GB5009.5-2010—Determination of Protein in Foods", and the protein conversion factor is 6.24. The fat content of the product is determined according to the method of GB/T5009.6. The water content in the product is determined according to the method of GB/T5009.3. The lead content in the product is determined according to the methods of GB5009.12, GB5009.17 and GB5009.11. The mercury content in the product is determined according to the method. The arsenic content in the product is determined according to the method. The aflatoxin content in the product is determined according to the method of GB5009.23. The total bacterial count and the amounts of coliform, mold and pathogenic bacteria in the product are respectively determined according to the methods of GB4789.2, GB4789.3, GB4789.15 and GB4789.4.

In the present invention, the optical density value of the protein is determined by the following method (as shown in FIG. 4): the prepared 10% (v/v) β-mercaptoethanol-added sample is subjected to reducing SDS polyacrylamide gel electrophoretograms by using a 15% (w/v) separation gel, and the gel after electrophoretograms is stained with Coomassie brilliant blue staining (the lower parts of FIGS. 4A-E). The bands in the gel are subjected to densitometric analysis by using Quantity One software to produce signal peaks (the upper parts in FIGS. 4A-E). The area of the signal peak is a functional relationship between the optical density value and the protein content of the component protein. Specifically, the optical density values of the different prolamin components are recorded as Di (i=1,2,3, ..., n), and the ratio of the prolamin components to the percentage of the optical density value of the prolamin is calculated, i.e., Di/D0%.

Figure 4A:
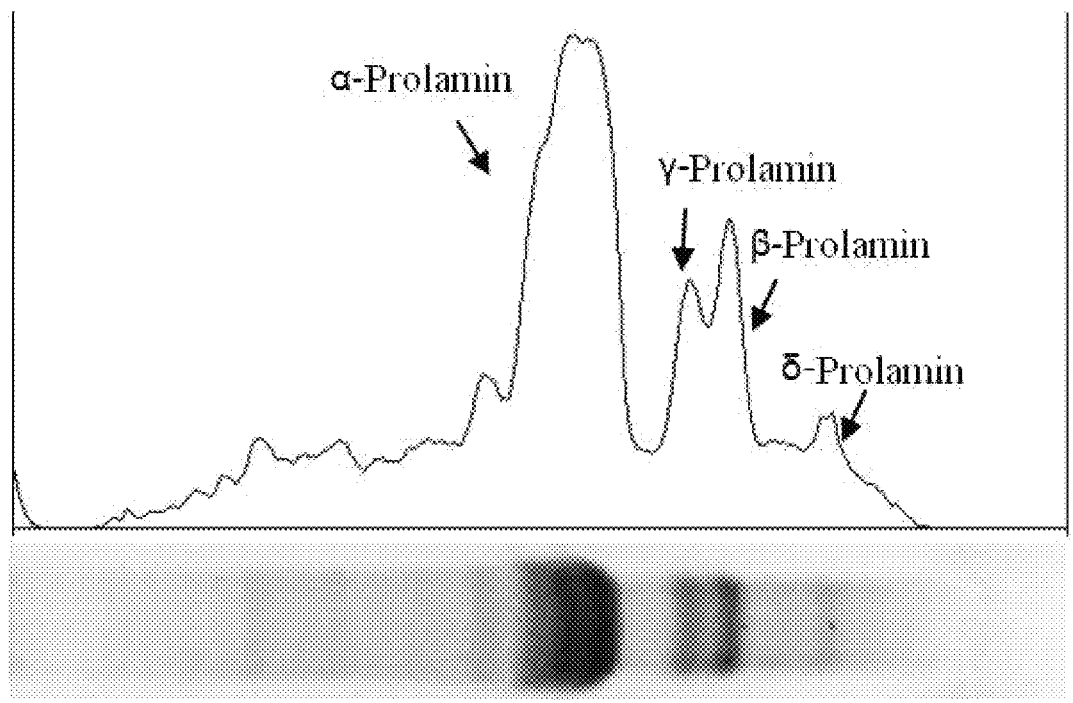
FIGS. 4A-4E are electrophoretograms (on the lower panel) and optical density analysis charts (on the upper panel) of the protein components in the exemplary raw material and different corn protein products after reducing sodium dodecyl sulfate (SDS) polyacrylamide gel electrophoretograms. Among them, A is the raw material; B is the α-prolamin product by ethanol extraction (traditional method); C is the α-prolamin product obtained by the method of the present invention; and D and E are prolamin composition products obtained by the method of the present invention.
Figure 4B:
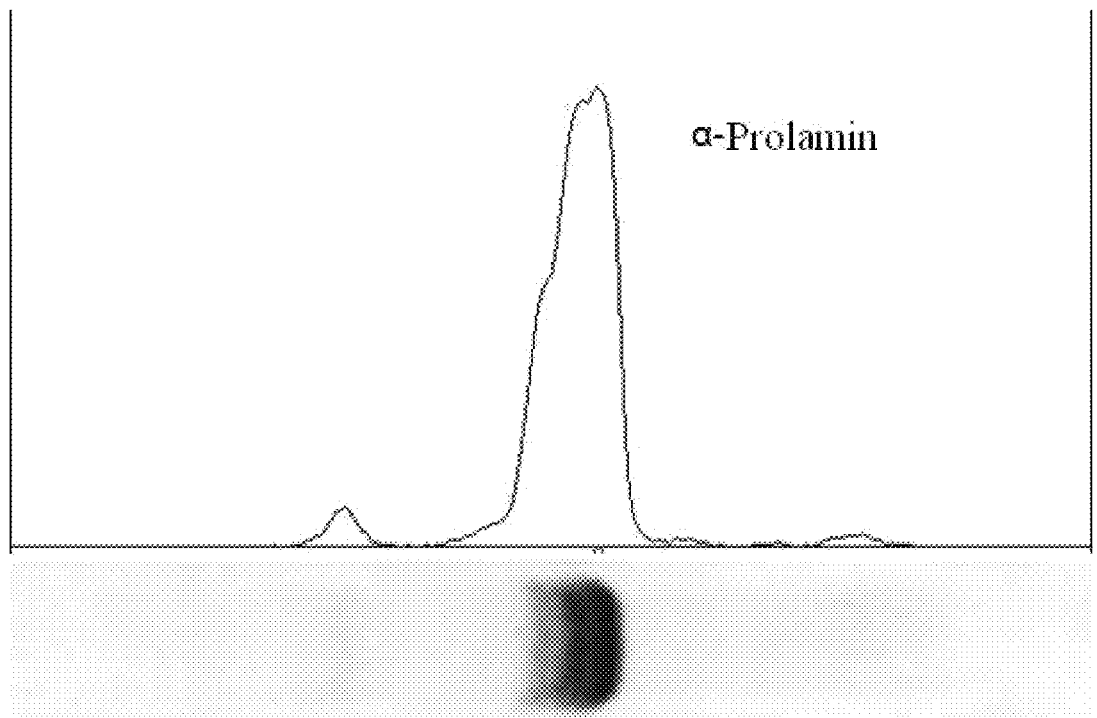

According to an exemplary implementation, the prolamin-containing extraction material used in the present invention may have, for example, an electrophoretograms and an optical density spectrum thereof of α-prolamin, β-prolamin, γ-prolamin and δ-prolamin in FIG. 4A.

Figure 4C:
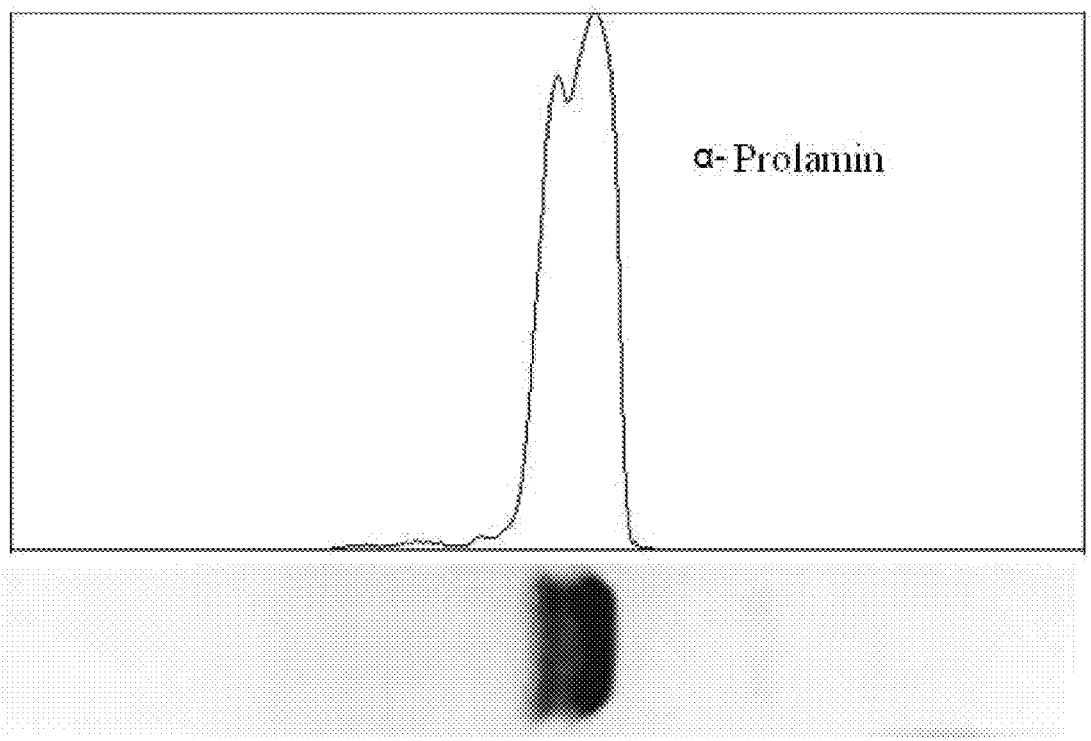

According to an exemplary implementation, the prolamin product of the present invention may have an electrophoretograms and an optical density spectrum thereof of α-prolamin in FIG. 4C.

Figure 4D:
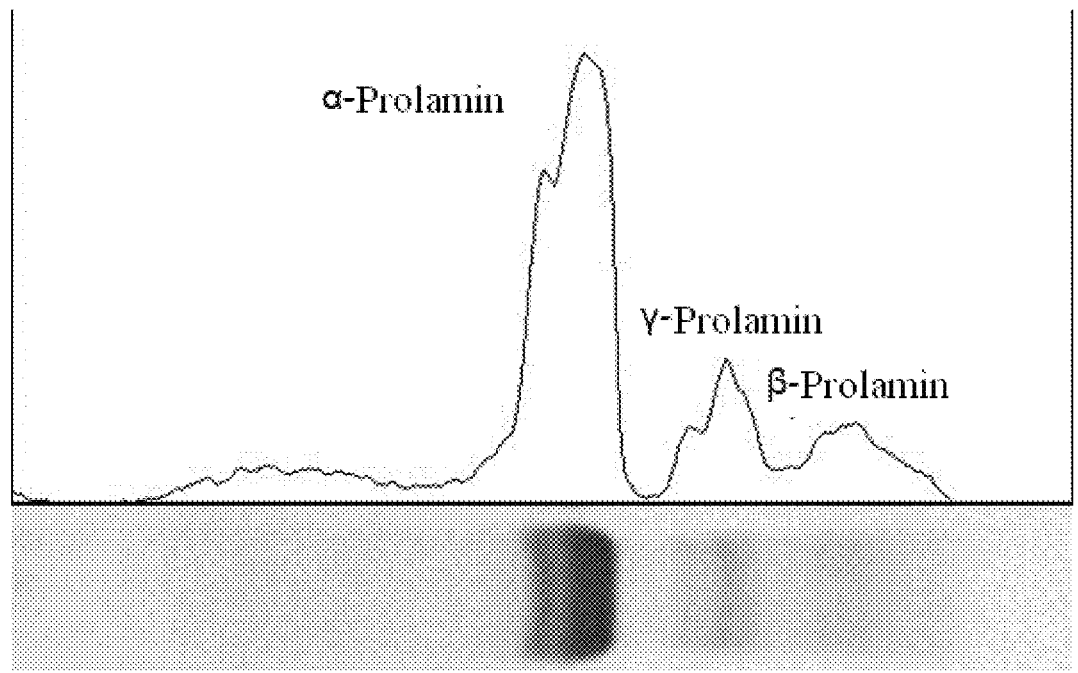
Figure 4E:
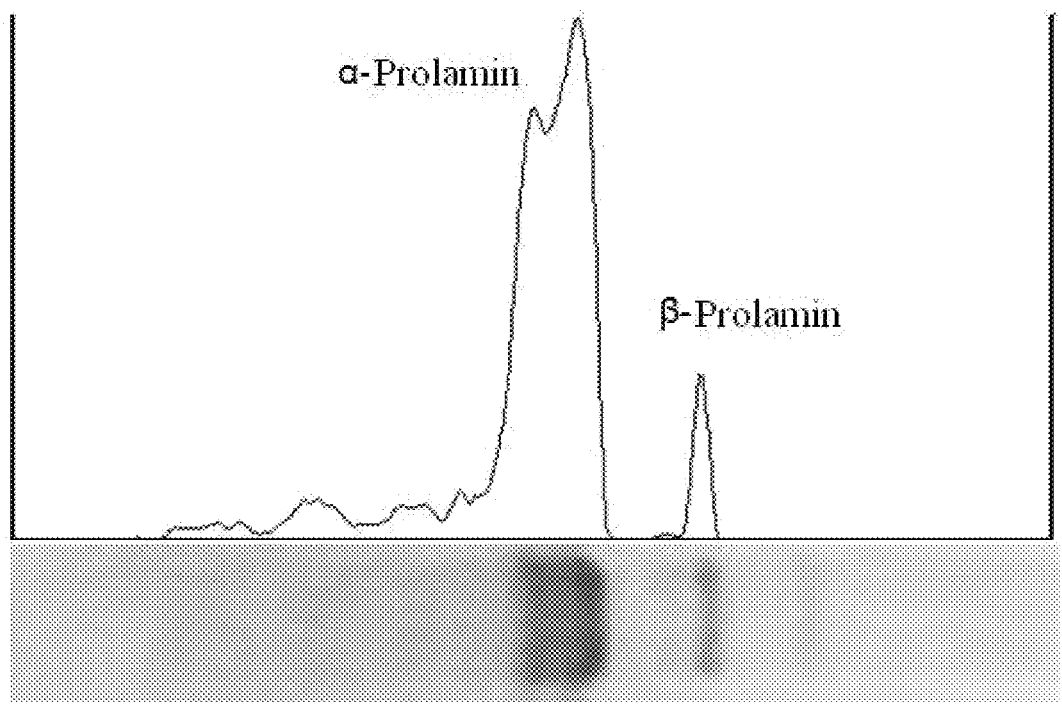

According to an exemplary implementation, the prolamin product of the present invention may have an electrophoretogram and an optical density spectrum thereof of α-prolamin, β-prolamin and γ-prolamin in FIG. 4D.

According to an exemplary implementation, the prolamin product of the present invention may have an electrophoretogram and an optical density spectrum thereof of α-prolamin and β-prolamin in FIG. 4A.

According to an exemplary implementation, the alkaline protease used in the present invention is a *Bacillus* serine protease. According to an exemplary implementation, the acidic protease used in the present invention is a mold carboxyl protease. According to an exemplary implementation, the neutral protease used in the present invention is a mold or *Bacillus* serine metalloproteinase. According to an exemplary implementation, the thiol protease used in the present invention is a plant-derived (such as pineapple fruit stem, leaf and skin and papaya fruit) thiol protease, for example, bromelain and papain.

In the reagent compositions listed in Table 1 above, acids and alkalis are used to adjust the reaction to a suitable acid-base environment and are also used to adjust the dissolved state of the components. The sulfur-containing compound, phosphorus-containing compound and metal ion are mainly used for adjusting the structure of the protein substrate; and the metal ion and chelator are used for adjusting the activity or stability of the protease, carbohydrase and other enzymes. Those skilled in the art, in light of the teachings of the present invention, are fully capable of understanding how the appropriate reagent composition and its concentration should be selected according to the enzyme actually employed and the corresponding substrate to achieve the objectives of the present invention (for example, those skilled in the art can appropriately select the enzyme treatment time and control the hydrolysis time by the prior art knowledge to achieve the desired degree of hydrolysis of the substrate, thereby implementing the removal of the hydrolysate by filtration by the difference in particle size in the present invention).

EXAMPLES

In addition to other descriptions, the percentages indicated in the present invention are all by weight. In the following examples, if only the concentration is indicated when the relevant reagent is added, it indicates the concentration reached by the reagent after it is added to the system. All reactions are carried out under normal pressure unless otherwise stated.

Example 1

The corn gluten meal containing 8.9% water and 64% protein (dry-basis) is adjusted to a water content of 70%, then introduced into an enzymolysis tank to adjust to pH 4.8 and 45° C., added with acidic protease (MA-SD, Amano Enzyme China Ltd.) accounting for 4.8% of the protein and 60 mM tris(2-carboxyethyl)phosphine to react for 1.2 hours and be adjusted to pH 7.5 and 52° C., added with 2.6% alkaline protease (2709, Pangbo Bioengineering Co., Ltd.), 2% neutral protease (SUKAPro NE, Sukehan Bioengineering Co., Ltd.) and 1 mM mercaptoethanol to react for 0.5 hour, centrifuged and washed, and the precipitate is collected. In the obtained product, the total protein (dry-basis) content is 61.1%; and in the protein, the prolamin content is greater than 74%, the α-prolamin content is 95%, and the β-prolamin content is 2%.

Example 2

The corn gluten meal containing 62.4% water and 70% protein (dry-basis) is adjusted to a water content of 75%, then introduced into an enzymolysis tank to adjust to pH 3.8 and 35° C., added with acidic protease (SUKAPro AC Sukahan Bio-Technology Co., Ltd.) accounting for 0.38% by weight of the protein, 0.26% bromelin (food grade, Pangbo Bioengineering Co., Ltd.), 50 mM sodium metabisulfite, 0.5 mM tris(2-carboxyethyl)phosphine and 4 mM manganese ion to react for 10 hours, heated to 50° C. and held for 0.5 hour, adjusted to pH 8.3 and 52° C., added with 0.33% alkaline protease (2709, Pangbo Bioengineering Co., Ltd.) to react for 1 hour, added 10 mM EDTA, centrifuged and washed, and the precipitate is collected. In the obtained product, the total protein (dry-basis) content is 54.1%; and in the protein, the prolamin content is 97.55%, wherein the α-prolamin content is 95.85%, the β-prolamin content is 1.9%, and the γ-prolamin content is 0.95%.

Example 3

The corn gluten meal material containing 89.9% water and 68% protein (dry-basis) is adjusted to a water content of 80%, then introduced into an enzymolysis tank to adjust to pH 6.5 and 45° C., added with papain (food grade, Pangbo Bioengineering Co., Ltd.) accounting for 0.01% of the protein, 20 mM mercaptoethanol and 0.01 mM cobalt ion to react for 1.5 hours, adjusted to pH 10.2 and 45° C., added with 0.01% alkaline protease (Protex 6L, Genencor Bioengineering Co., Ltd.) to react for 2 hours, centrifuged and washed, and the precipitate is collected. In the obtained product, the total protein (dry-basis) content is 55.9%; and in the protein, the prolamin content is greater than 90.66%, wherein the α-prolamin content is 85.54%, the β-prolamin content is 9.91%, and the γ-prolamin content is 4.34%.

Example 4

The dried distillers' grains (DDG) containing 9.0% water and 28% protein (dry-basis) is adjusted to a water content of 80%, introduced into an enzymolysis tank, added with acidic protease (MA-SD, Amano Enzyme China Ltd.) accounting for 0.8% by weight of the protein and 40 mM tris(2-carboxyethyl)phosphine under the conditions of pH 4.2 and 35° C. to react for 6 hours, adjusted to pH 6.5 and 45° C., added with 0.5% neutral protease (1398, Pangbo Bioengineering Co., Ltd.), 1.7% papain (food grade, Pangbo Bioengineering Co., Ltd.), 5 mM mercaptoethanol and 0.1 mM zinc ion to react for 0.5 hour, centrifuged and washed, and the precipitate is collected. In the obtained product, the total protein (dry-basis) content is 23.9%; and in the protein, the prolamin content is 81.30%, wherein the α-prolamin content is 94.5%, the β-prolamin content is 1.95%, and the γ-prolamin content is 0.04%.

Example 5

The dried distillers' grains with solubles (DDGS) containing 11.0% water and 30% protein (dry-basis) are adjusted with water, washed with water twice, adjusted to a water content of 95%, added with acidic protease (SUKAPro NE, Sukehan Bioengineering Co., Ltd.) accounting for 0.23% by weight of the protein and 2 mM tris(2-carboxyethyl)phosphine under the conditions of pH 4.8 and 55° C. to react for 0.5 hour, added with bromelin (food grade, Pangbo Bioengineering Co., Ltd.) accounting for 0.3% by weight of the protein under the conditions of pH4.8 and 53° C. to react for 2.8 hours, adjusted to pH 7.2, added with 0.5% neutral protease (1398, Pangbo Bioengineering Co., Ltd.) at 53° C., 6 mM calcium ion, 15 mM mercaptoethanol and 15 mM cysteine to react for 3.1 hours, centrifuged and washed, and the precipitate is collected. In the obtained product, the total protein (dry-basis) content is 24.3%; and in the protein, the α-prolamin content is 87.5%, the β-prolamin content is 3.1%, and the γ-prolamin content is 5.1%.

Example 6

The wet distillers' grains (WDG) containing 31.0% water and 32% protein are adjusted with water to a water content of 80%, added with neutral protease (SUKAPro NE, Sukehan Bioengineering Co., Ltd.) accounting for 0.04% by weight of the protein, 2 mM magnesium ion, 2 mM calcium ion and 20 mM mercaptoethanol under the conditions of pH 7.5 and 25° C. to react for 4.5 hours, and adjusted to pH 10.1 and held for 0.2 hour. The mixture is filtered by a 1 μm pore size filter membrane to obtain a first permeate and a retentate, the retentate is adjusted to a water content of 80%, introduced back to an enzymolysis tank to adjust to pH 10.1 and 55° C., added with alkaline protease(2709, Pangbo Bioengineering Co., Ltd.) accounting for 0.02% by weight of the protein in the material, held for 0.5 hour, centrifuged and washed, and the precipitate is collected. In the obtained product, the total protein (dry-basis) content is 25.7%; and in the protein, the prolamin content is greater than 93.1%, wherein the α-prolamin content is 77.9%, the β-prolamin content is 17.2%, and the γ-prolamin content is 1.3%.

Examples 7-12 use the following materials: the corn gluten meal with a water content of 80% is added with acidic protease (MA-SD, Amano Enzyme China Ltd.) accounting for 2% by weight of the protein and 10 mM tris(2-carboxyethyl)phosphine under the conditions of pH 4.2 and 35° C. to react for 3 hours, adjusted to pH 6.5 and 45° C., and added with 0.5% neutral protease (1398, Pangbo Bioengineering Co., Ltd) and 1.7% papain (food grade, Pangbo Bioengineering Co., Ltd.) to react for 1 hour.

Example 7

The above-mentioned material is milled (grinding disk gap of about 40 μm) by a colloid mill (MagicLab, IKA), introduced into an enzymolysis tank to adjust to pH 5.0 and 63° C., added with α-amylase (Spezyme Fred, Genencor Bioengineering Co., Ltd.) accounting for 8% by weight of the starch and 4% glucoamylase (Spirizyme Ultra, Novozymes Biotehcnology Co., Ltd.) to react for 2 hours; and the mixture is centrifuged at 200 g for 15 min (ALLEGRA 30R, US Beckman Coulter Co., Ltd.), the precipitate is collected, adjusted to a water content of 70%, introduced into a second enzymolysis tank to adjust to pH 5.5 and 50° C., added with cellulase (SUKAZYM-SUKACell, Sukehan Bioengineering Co., Ltd.) accounting for 3.0% by weight of the fiber, 2% composite enzymes (Viscozyme L, Novozymes Biotehcnology Co., Ltd.) including arabanase, cellulase, β-glucanase, hemicellulase xylanase and the like, 10 mM calcium ion and 10 mM potassium ion to react for 2 hours, filtered by a 50 μm pore size cloth filter (the average particle size of the target phase containing protein is about 100 μm, and the average particle size of non-target phase components with different particle sizes is mostly less than 30 μm (including solubles)) to obtain a first filter cake, the first filter cake is adjusted to a water content of 70%, pH 7.5 and 55° C., added with 35 mM EDTA and filtered by a 10 μm membrane (the average particle size of the target phase containing protein is about 15 μm, and most non-target phases are solubles) to obtain a second filtrate and a filter cake, and the obtained filter cake is washed and dried to obtain a corn protein product with the protein (dry-basis) content of 88.4%.

Example 8

The above-mentioned material is milled (grinding disk gap of about 2 μm) by a colloid mill (MagicLab, IKA), adjusted with water to a water content of 75%, introduced into a first enzymolysis tank to adjust to pH 3.0 and 35° C., added with α-amylase (Liquozyme SCDS, Novozymes Biotehcnology Co., Ltd.) accounting for 1% by weight of the starch and 1 wt % composite amylase (Novozyme NS 50013, Novozymes Biotehcnology Co., Ltd.) composed of saccharifying enzyme and pullulanase to react for 7 hours, filtered by a 1 μm pore size filter screen (the average particle size of the target phase containing protein is about 150 μm, and the average particle size of different components of non-target phases with different particle sizes is mostly less than 2 μm (including solubles)) to obtain a first filter cake, and the first filter cake is adjusted to a water content of 75%; and the material is introduced into a third enzymolysis tank to adjust to pH 6.5 and 45° C., added with cellulase accounting for 12% by weight of the fiber and 5% β-glucanase (Ultraflo, Novozymes Biotehcnology Co., Ltd., mainly comprising β-glucanase and further comprising xylanase and the like) and 13% composite enzyme (Viscozyme L, Novozymes Biotehcnology Co., Ltd.) to react for 4 hours, added with 10 mM EDTA, adjusted to pH 5.0, filtered by a 40 μm pore size cloth filter (the average particle size of the target phase containing protein is about 110 μm, and the average particle size of non-target phase components with different particle sizes is mostly less than 30 μm (including solubles)) to obtain a second filtrate and a filter cake, and the filter cake is washed and dried to obtain a corn protein product with the protein (dry-basis) content of 99.2%.

Example 9

The above-mentioned material is milled (grinding disk gap of about 10 μm) by a colloid mill (MagicLab, IKA), introduced into a first enzymolysis tank to adjust to pH 4.0 and 40° C., and added with cellulase (Celluclast, Novozymes Biotehcnology Co., Ltd.) accounting for 0.2% by weight of the fiber, 0.4% composite enzyme (Viscozyme L, Novozymes Biotehcnology Co., Ltd.) and 0.01 mM potassium ion to react for 8 hours. The mixture is filtered by a 80 μm pore size cloth filter (the average particle size of the target phase containing protein is about 140 μm, and the average particle size of different components of the non-target phases is mostly less than 9 μm (including solubles)) to obtain a first filtrate and a filter cake, the first filter cake is adjusted to a water content of 80%, introduced into a second enzymolysis tank to adjust to pH 6.5 and 45° C., added with α-amylase (Spezyme Fred, Genencor Bioengineering Co., Ltd.) accounting for 0.1% by weight of the starch, 0.05% saccharifying enzyme (Spirizyme Ultra, Novozymes Biotehcnology Co., Ltd.) and 0.1% pullulanase (Promozyme D2, Novozymes Biotehcnology Co., Ltd.), heated to 72° C. and held for 5 hours, adjusted to pH 10.5, filtered by a 20 nm pore size filter membrane (the average particle size of the target phase containing protein is about 0.5 μm, and most non-target phases are solubles) to obtain a second permeate and a retentate, and the retentate is washed and dried to obtain a corn protein product with the protein (dry-basis) content of 85.7%.

Example 10

The above-mentioned material is milled (grinding disk gap of about 100 μm) by a colloid mill (MagicLab, IKA), adjusted to a water content of 80%, introduced into a first enzymolysis tank, added with a composite cellulase (Viscozyme L, Novozymes Biotehcnology Co., Ltd.) accounting for 0.2% by weight of the fiber and 0.1 mM EDTA under the conditions of pH 4.5 and 60° C. to react for 12 hours, centrifuged, washed with water once and adjusted to a water content of 80%; and the mixture is adjusted to pH 8, added with a composite amylase (Spirizyme Excel, Novozymes Biotehcnology Co., Ltd.) accounting for 0.05% by weight of the starch at 45° C. and held for 10 hours, filtered by a 80 µm pore size cloth filter (the average particle size of the target phase containing protein is about 5 µm, and the average particle size of different components of the non-target phases is mostly greater than 90 µm) to obtain a first filtrate and a filter cake, and the first filtrate passes through a 100 nm microfiltration membrane (the average particle size of the target phase containing protein is about 5 µm, and most non-target phases are solubles) to obtain a second filtrate. The second retentate is centrifuged at 1000 g for 10 min to obtain a precipitate, and the precipitate is washed and dried to obtain a corn protein product with the protein (dry-basis) content of 75.8%.

Example 11

The above-mentioned material is milled (grinding disk gap of about 150 µm) by a colloid mill (MagicLab, IKA), introduced into a first enzymolysis tank, added with cellulase (Celluclast, Novozymes Biotehcnology Co., Ltd.) accounting for 12% by weight of the fiber, 8 wt % β-glucanase (Ultraflo, Novozymes Biotehcnology Co., Ltd.) and 12 mM calcium ion under the conditions of pH 5 and 55° C. to react for 0.5 hour; and the mixture is filtered by a 10 µm pore size filter membrane (the average particle size of the target phase containing protein is about 110 µm, and most non-target phases are solubles) to obtain a first permeate and a retentate, the retentate is adjusted to a water content of 85%, introduced into a second enzymolysis tank, adjusted to pH 7.5, added with α-amylase (Spezyme Fred, Genencor Bioengineering Co., Ltd.) accounting for 1% by weight of the starch, 1% saccharifying enzyme (Spirizyme Ultra, Novozymes Biotehcnology Co., Ltd.), 3% composite amylase (Spirizyme Excel, Novozymes Biotehcnology Co., Ltd.) and 18 mM EGTA at 50° C. to react for 3.5 hours and filtered by a 50 µm pore size cloth filter (the average particle size of the target phase containing protein is about 15 µm and soluble substances, and the average particle size of different components of the non-target phases is mostly greater than 140 µm) to obtain a second permeate and a filter cake, the permeate is centrifuged at 2000 g for 10 min, and the obtained solid phase is washed and dried to obtain a corn protein product with the protein (dry-basis) content of 80.0%.

Example 12

The above-mentioned material is milled to a particle size of about 30 µm, introduced into a first enzymolysis tank, and added with α-amylase (Liquozyme SCDS, Novozymes Biotehcnology Co., Ltd.) accounting for 5% by weight of the starch, 3 wt % saccharifying enzyme (Spirizyme Ultra, Novozymes Biotehcnology Co., Ltd.), 2 wt % pullulanase (Promozyme D2, Novozymes Biotehcnology Co., Ltd.), 10% composite amylase (Novozyme NS50013, Novozymes Biotehcnology Co., Ltd.) and 2 mM calcium ion under the conditions of pH 3.5 and 30° C. to react for 1 hour; the mixture is adjusted to pH 5.6, and added with composite cellulase (GC 518, Genencor Bioengineering Co., Ltd.) accounting for 10% by weight of the fiber at 50° C. to react for 5 hours; and the mixture is filtered by a 1 µm pore size filter membrane (the average particle size of the target phase containing protein is mostly greater than 100 µm, and most non-target phases are solubles) to obtain a first permeate and a retentate, the retentate is adjusted to a water content of 80%, introduced into a slurrying tank and adjusted to pH 10 and 55° C. and passes through a 20 µm filter screen (the average particle size of the target phase containing protein is about 1 µm, and the average particle size of different components of the non-target phases is about 29 µm) to obtain a second filtrate and a retentate, and the filtrate is dried to obtain a corn protein product with the protein (dry-basis) content of 95.0%.

Examples 13 and 14 use the following raw material: the corn gluten meal with a water content of 80% is adjusted to pH 5.6 and added with composite cellulase accounting for 8% by weight of the fiber and 2.0% cellulase at 50° C. to react for 2 hours, or the corn gluten meal is degraded under other conditions such that the fiber is about one-tenth of the original fiber.

Example 13

The above-mentioned material is milled by a colloid mill (grinding disk gap of about 20 µm), the milled material is adjusted respectively to pH 3, 4 and 6.2 and filtered by a 10 µm pore size filter membrane to obtain a retentate, and the retentate is centrifuged and dried to respectively obtain products with the protein content of 71.25%, 70.76% and 70.36%; and when a 48 µm pore size filter screen is used for filtration to obtain a filter cake, the filter cake is dried to respectively obtain products with the protein content of 77.7%, 76.8% and 76.3%. After the material with pH 4 in the present example is treated by a 0.1 µm pore size filter membrane or a 75 µm or 150 µm pore size filter screen, the obtained retentate or filter cake is further dewatered and dried to respectively obtain protein products with the protein content of 69.9%, 76.4% and 71.9%.

Example 14

The above-mentioned material is respectively adjusted to pH 6.9, 8 and 10.5, filtered by a 1 µm pore size filter membrane to obtain a permeate, and the permeate is centrifuged and dried to respectively obtain protein products with the protein content of 93.2%, 96.0% and 97.5%; and when a 75 µm pore size filter screen is used for filtration to obtain a filter cake, the filter cake is dried to respectively obtain products with the protein content of 76.9%, 78.8% and 79.7%. After the material with pH 8 in the present example is treated by a 0.1 µm pore size filter membrane or a 38 µm or 150 µm pore size filter screen, the obtained retentate or filter cake is further dewatered and dried to respectively obtain protein products with the protein content of 99.5%, 87.2% and 72.2%.

Examples 15 and 16 use the following raw material: the corn gluten meal with a water content of 80% is adjusted to pH 6.5 and 45° C., added with α-amylase accounting for 2% by weight of the starch, 1% saccharifying enzyme and 2% pullulanase, heated to 72° C. and held for 2.5 hours; or the corn gluten meal is treated under other conditions such that the liquefied starch is one half of the original starch, adjusted to pH 5.6, and added with composite cellulase accounting for 8% by weight of the fiber and 2.0% cellulase at 50° C. to react for 2 hours; or the corn gluten meal is degraded under other conditions such that the fiber is about one-tenth of the original fiber.

Example 15

The above-mentioned material is milled by a colloid mill (grinding disk gap of about 20 µm), the milled material is adjusted respectively to pH 3, 4 and 6.2 and filtered by a 10 µm pore size filter membrane to obtain a retentate, and the retentate is centrifuged and dried to respectively obtain products with the protein content of 79.0%, 78.7% and 78.3%; and when a 48 µm pore size filter screen is used for filtration to obtain a filter cake, the filter cake is dried to respectively obtain products with the protein content of 83.6%, 83.0% and 82.63%. After the material with pH 4 in the present example is treated by a 0.1 µm pore size filter membrane or a 75 μm or 150 μm pore size filter screen, the obtained retentate or filter cake is further dewatered and dried to respectively obtain protein products with the protein content of 78.0%, 82.7% and 79.4%.

Example 16

The above-mentioned material is respectively adjusted to pH 6.9, 8 and 10.5, filtered by a 1 μm pore size filter membrane to obtain a permeate, and the permeate is centrifuged and dried to respectively obtain protein products with the protein content of 95.9%, 97.4% and 98.2%; and when a 75 μm pore size filter screen is used for filtration to obtain a filter cake, the filter cake is dried to respectively obtain products with the protein content of 84.8%, 86.1% and 86.8%. After the material with pH 8 in the present example is treated by a 0.1 μm pore size filter membrane or a 38 μm or 150 μm pore size filter screen, the obtained retentate or filter cake is further dewatered and dried to respectively obtain protein products with the protein content of 99.5%, 92.3% and 80.0%.

Example 17

The corn gluten meal containing 8.9% water is milled by a jet mill (FQS15, Shanghai Zhikai Powder Machinery manufacturing Co., Ltd.) to a particle size of about 40 μm, and adjusted with water to a water content of 50% for sufficient hydration, and enters an enzymolysis and separation system: the material firstly enters a first enzymolysis tank to adjust to pH 5.0 and 63° C., and added with α-amylase (Spezyme Fred, Genencor Bioengineering Co., Ltd.) accounting for 8% by weight of the starch and 4% saccharifying enzyme (Spirizyme Ultra, Novozymes Biotehcnology Co., Ltd.) to react for 2 hours; and the mixture is centrifuged at 200 g for 15 min (ALLEGRA 30R, US Beckman Coulter Co., Ltd.), the precipitate is collected, adjusted to a water content of 70%, introduced into a second enzymolysis tank to adjust to pH 5.5 and 50° C., added with cellulase (SUKAZYM-SUKACell, Sukehan Bioengineering Co., Ltd.) accounting for 3.0% by weight of the fiber, 2% composite enzyme (Viscozyme L, Novozymes Biotehcnology Co., Ltd.), 10 mM calcium ion and 10 mM potassium ion to react for 2 hours, filtered by a 50 μm pore size cloth filter to obtain a first filter cake, and the first filter cake is adjusted to a water content of 70%, introduced into a third enzymolysis tank, adjusted to pH 4.8 and 35° C., added with acidic protease (carboxyl protease MA-SD, Amano Enzyme China Ltd.) accounting for 5% of the protein and 60 mM tris(2-carboxyethyl)phosphine to react for 1.5 hours, adjusted to pH 7.5 and 55° C., added with 3% alkaline protease (serine protease 2709, Pangbo Bioengineering Co., Ltd.), 2% neutral protease (metalloproteinase SUKAPro NE, Sukehan Bioengineering Co., Ltd.) and 1 mM mercaptoethanol to react for 0.5 hour, added with 35 mM EDTA, and filtered by a 10 μm membrane to obtain a second filtrate and a filter cake. The obtained filter cake is washed and dried to obtain a zein product with the protein (dry-basis) content of 90%, wherein the prolamin content in the protein is greater than 74%, all the prolamin is α-prolamin (100%), and the fat and ash (dry-basis) contents are respectively 1.04% and 4.01%. In addition, the second filtrate is filtered by a 1 μm microfiltration membrane, and the retentate is refined, dewatered and dried to obtain a product with the protein (dry-basis) content of 86%.

Example 18

The corn gluten meal containing 62.4% water is milled (roller gap of about 2 μm) by a rolling press (S120, Changzhou Zili Chemical Machinery Co., Ltd.) and adjusted with water to a water content of 75%, and enters an enzymolysis and separation system: the material firstly enters a first enzymolysis tank to adjust to pH 3.0 and 35° C., added with α-amylase (Liquozyme SCDS, Novozymes Biotehcnology Co., Ltd.) accounting for 1% by weight of the starch and 1 wt % composite amylase (Novozyme NS 50013, Novozymes Biotehcnology Co., Ltd.) comprising saccharifying enzyme and pullulanase to react for 7 hours, filtered by a 1 μm pore size filter screen to obtain a first filter cake, and adjusted to a water content of 75%; the mixture is introduced to a second enzymolysis tank to adjust to pH 3.8 and 35° C., added with acid protease (carboxyl protease SUKAPro AC, Sukehan Bioengineering Co., Ltd.) accounting for 0.4% by weight of the protein, 0.3% bromelin (food grade, Pangbo Bioengineering Co., Ltd.), 50 mM sodium metabisulfite, 0.5 mM tris(2-carboxyethyl)phosphine and 4 mM manganese ion to firstly react for 10 hours, heated to 50° C. and held for 0.5 hour, adjusted to pH 8.5 and 65° C., added with 0.3% alkaline protease (serine protease 2709, Pangbo Bioengineering Co., Ltd.) to react for 1 hour and centrifuged at 150000 g for 10 s (Optima™ XE, US Beckman Coulter Co., Ltd.), and the precipitate is collected and adjusted to a water content of 75%; and the material is introduced into a third enzymolysis tank to adjust to pH 6.5 and 45° C., added with cellulase accounting for 12% by weight of the fiber and 5% β-glucanase (Ultraflo, Novozymes Biotehcnology Co., Ltd.) and 13% composite enzyme (Viscozyme L, Novozymes Biotehcnology Co., Ltd.) to react for 4 hours, added with 10 mM EDTA, adjusted to pH 5.0, filtered by a 40 μm pore size cloth filter to obtain a second filtrate and a filter cake, and the filter cake is washed and dried to obtain a zein product with the protein (dry-basis) content of 99.1%, in which the prolamin content is greater than 98.4%, wherein the α-prolamin content is 97%, the β-prolamin content is 2%, the γ-prolamin content is 1%, and the fat and ash (dry-basis) contents are respectively 0.5% and 0.2%. In addition, the second filtrate is filtered by a 1 μm microfiltration membrane, and the retentate is refined, dewatered and dried to obtain a product with the protein (dry-basis) content of 75.1%.

Example 19

The corn gluten meal containing 89.9% water is milled (grinding disk gap of about 10 μm) by a colloid mill (MagicLab, IKA) and introduced into an enzymolysis and separation system: the material firstly enters a first enzymolysis tank to adjust to pH 4.0 and 40° C., and is added with cellulase (Celluclast, Novozymes Biotehcnology Co., Ltd.) accounting for 0.2% by weight of the fiber, 0.4% composite enzyme (Viscozyme L. Novozymes Biotehcnology Co., Ltd.) and 0.01 mM potassium ion to react for 8 hours. The mixture is filtered by a 80 μm pore size cloth filter to obtain a first filtrate and a filter cake, the first filtrate is filtered by a 1 μm microfiltration membrane to obtain a second filtrate, the second filtrate is filtered by a 10 nm ultrafiltration membrane to obtain a third retentate, and the first filter cake and the third retentate are combined, adjusted to a water content of 80%, introduced into a second enzymolysis tank, adjusted to pH 8.0 and 45° C., added with alkaline protease (Protex 6L, Genencor Bioengineering Co., Ltd.) accounting for 0.4% by weight of the protein and 20 mM mercaptoethanol to react for 1.5 hours, added with α-amylase (Spezyme Fred, Genencor Bioengineering Co., Ltd.) accounting for 0.1% by weight of the starch, 0.05% saccharifying enzyme (Spirizyme Ultra, Novozymes Biotehcnology Co., Ltd.) and 0.1% pullulanase (Promozyme D2, Novozymes Biotehcnology Co., Ltd.), heated to 72° C. and held for 5 hours; and the material is introduced into a third enzymolysis tank to adjust to pH 10.5 and 45° C. to react for 0.5 hour, filtered by a 20 nm pore size filter membrane to obtain a fourth permeate and a retentate, and the retentate is washed, dewatered and dried to obtain a zein product with the protein (dry-basis) content of 85%, in which the prolamin content is greater than 92%, wherein the α-prolamin content is 91%, the β-prolamin content is 7%, the γ-prolamin content is 2%, and the fat and ash (dry-basis) contents are respectively 3.2% and 1.52%. In addition, the fourth permeate is refined to obtain a product with the protein (dry-basis) content of 94.7%.

Example 20

The dried distiller's grains (DDG) containing 9.0% water are milled by a jet mill (FQS15, Shanghai Zhikai Powder Machinery manufacturing Co., Ltd.) to a particle size of about 100 μm, adjusted with water to a water content of 80%, and introduced into an enzymolysis and separation system: the material firstly enters a first enzymolysis tank, added with composite cellulase (Viscozyme L, Novozymes Biotehcnology Co., Ltd.) accounting for 0.2% by weight of the fiber and 0.1 mM EDTA under the conditions of pH 4.5 and 60° C. to react for 12 hours, centrifuged, washed with water once, and adjusted to a water content of 80%; the material is introduced into a second enzymolysis tank, added with acidic protease (MA-SD, Amano Enzyme China Ltd.) accounting for 1% by weight of the protein and 40 mM tris(2-carboxyethyl)phosphine under the conditions of pH 4.2 and 35° C. to react for 6 hours, adjusted to pH 6.5 and 45° C., added with 0.5% neutral protease (1398, Pangbo Bioengineering Co., Ltd.), 1.5% papain (food grade, Pangbo Bioengineering Co., Ltd.), 5 mM mercaptoethanol and 0.1 mM zinc ion to react for 0.5 hour, adjusted to pH 8, added with composite amylase (Spirizyme Excel, Novozymes Biotehcnology Co., Ltd.) accounting for 0.05% by weight of the starch at 45° C., held for 10 hours, and filtered by a 80 μm pore size cloth filter to obtain a first filtrate and a filter cake, and the first filtrate is filtered by a 100 nm microfiltration membrane to obtain a second filtrate. The second retentate is centrifuged at 1000 g for 10 min to obtain a precipitate, and the precipitate is washed and dried to obtain a zein product with the protein (dry-basis) content of 75%, in which the prolamin content is greater than 81.50%, wherein the α-prolamin content is 98%, the β-prolamin content is 1.99%, the γ-prolamin content is 0.03%, and the fat and ash (dry-basis) contents are respectively 4.98% and 2.11%. In addition, the second permeate and the first filter cake are combined and dried to obtain a product with the protein (dry-basis) content of 50%.

Example 21

The dried distillers' grains with solubles DDGS containing 11.0% water is adjusted with water, washed with water twice, adjusted to a water content of 95%, milled (grinding disk gap of about 150 μm) by a colloid mill (MagicLab, IKA), and introduced into an enzymolysis and separation system: the material firstly enters a first enzymolysis tank, added with cellulase (Celluclast, Novozymes Biotehcnology Co., Ltd.) accounting for 12% by weight of the fiber, 8 wt % β-glucanase (Ultraflo, Novozymes Biotehcnology Co., Ltd.), 12 mM calcium ion, acidic protease (SUKAPro AC, Sukehan Bioengineering Co., Ltd.) accounting for 0.2% by weight of the protein and 2 mM tris(2-carboxyethyl)phosphine under the conditions of pH 5 and 55° C. to react for 0.5 hour; and the mixture is filtered by a 10 μm pore size filter membrane to obtain a first permeate and a retentate, the retentate is adjusted to a water content of 85%, introduced into a second enzymolysis tank, added with bromelin (food grade, Pangbo Bioengineering Co., Ltd.) accounting for 0.3% by weight of the protein under the conditions of pH 5 and 50° C. to react for 3 hours, adjusted to pH 7.5, added with 0.5% neutral protease (1398, Pangbo Bioengineering Co., Ltd.), α-amylase (Spezyme Fred, Genencor Bioengineering Co., Ltd.) accounting for 1% by weight of the starch, 1% saccharifying enzyme (Spirizyme Ultra, Novozymes Biotehcnology Co., Ltd.), 3% composite amylase (Spirizyme Excel, Novozymes Biotehcnology Co., Ltd.), 15 mM mercaptoethanol, 15 mM cysteine and 18 mM EGTA at 50° C. to react for 3.5 hours, filtered by a 50 μm pore size cloth filter to obtain a second permeate and a filter cake, the permeate is centrifuged at 2000 g for 10 min, and the obtained solid phase is washed and dried to obtain a zein product with the protein (dry-basis) content of 79%, in which the prolamin content is greater than 85.60%, wherein the α-prolamin content is 87.5%, the β-prolamin content is 3.1%, the γ-prolamin content is 5.1%, and the fat and ash (dry-basis) contents are respectively 1.16% and 0.51%. In addition, the second filter cake is dried to obtain a product with the protein (dry-basis) content of 49%.

Example 22

The wet distillers' grains (WDG) containing 31.0% water is adjusted with water to a water content of 80%, milled (grinding disk gap of about 30 μm) by a colloid mill (MagicLab, IKA), and introduced into an enzymolysis and separation system: the material firstly enters a first enzymolysis tank, and is added with α-amylase (Liquozyme SCDS, Novozymes Biotehcnology Co., Ltd.) accounting for 5% by weight of the starch, 3 wt % saccharifying enzyme (Spirizyme Ultra, Novozymes Biotehcnology Co., Ltd.), 2 wt % pullulanase (Promozyme D2, Novozymes Biotehcnology Co., Ltd.), 10% composite amylase (Novozyme NS50013, Novozymes Biotehcnology Co., Ltd.), 2 mM magnesium ion and 2 mM calcium ion under the conditions of pH 3.5 and 30° C. to react for 1 hour; the mixture is adjusted to pH 5.6, and added with composite cellulase (GC 518, Genencor Bioengineering Co., Ltd.) accounting for 10% by weight of the fiber at 50° C. to react for 5 hours; and the material is introduced into a second enzymolysis tank, added with neutral protease (SUKAPro NE, Sukehan Bioengineering Co., Ltd.) accounting for 0.03% by weight of the protein and 20 mM mercaptoethanol under the conditions of pH 8 and 20° C. to react for 5 hours, adjusted to pH 10 and held for 0.2 hour. The mixture is filtered by a 1 μm pore size filter membrane to obtain a first permeate and a retentate, the retentate is adjusted to a water content of 80%, introduced into a third enzymolysis tank, adjusted to pH 10 and 55° C., added with alkaline protease (2709, Pangbo Bioengineering Co., Ltd.) accounting for 0.02% by weight of the protein in the material, held for 0.5 hour, filtered by a 20 μm filter screen to obtain a second filtrate and a retentate, and the filtrate is dried to obtain a zein product with the protein (dry-basis) content of 94.8%, in which the prolamin content is greater than 93.7%, wherein the α-prolamin content is 81.1%, the β-prolamin content is 17.6%, the γ-prolamin content is 1.3%, and the fat and ash (dry-basis) contents are respectively 2.48% and 0.70%. In addition, the second retentate is dried to obtain a product with the protein (dry-basis) content of 55%.

Comparative Example

The wet distillers' grains (WDG) containing 9.0% water is milled by a jet mill (FQS15, Shanghai Zhikai Powder Machinery manufacturing Co., Ltd.) to a particle size of about 100 μm, added with 70% ethanol and a 3.5% sodium hydroxide solution and extracted at 70° C. for 30 min. The ethanol solution accounts for 83% of the total weight of the liquid. The mixture is separated by a centrifuge (ALLEGRA 30R, US Beckman Coulter Co., Ltd.) to obtain a clear liquid (2000 g, 10 min), the clear liquid is filtered by a 1 micrometer pore size filter membrane, the filtrate is concentrated through a filter membrane with the molecular weight cutoff of 10 kDa, dried in a vacuum drying oven (DZF-6210, Shanghai Yiheng Scientific Instrument Co., Ltd.) and milled to obtain a 150-mesh product with the protein (dry-basis) content of 86.4%.

TABLE 2

Product composition of Examples 17-22

| Prolamin Product Composition | Example 17 | Example 18 | Example 19 | Example 20 | Example 21 | Example 22 | Comp. Example |
|---|---|---|---|---|---|---|---|
| Protein (dry-basis) Weight Percentage | 90.03% | 99.10% | 85.00% | 75.00% | 79.00% | 94.80% | 86.4% |
| Prolamin Content in Protein | 74.30% | 98.40% | 92.02% | 81.50% | 85.60% | 93.70% | 85.1% |
| α-prolamin Content in Prolamin | 100.00% | 97.00% | 91.00% | 98.00% | 87.50% | 81.10% | 89.5% |
| β- and γ-prolamin Content in Prolamin | 0.00% | 3.00% | 9.00% | 2.02% | 8.20% | 18.90% | 5.0% |
| β-prolamin Content in Prolamin | 0.00% | 2.00% | 7.00% | 1.99% | 3.10% | 17.60% | 3.0% |
| Fat (dry-basis) Weight Percentage | 1.04% | 0.50% | 3.20% | 4.98% | 1.16% | 2.48% | 5.1% |
| Ash (dry-basis) Weight Percentage | 4.01% | 0.20% | 1.52% | 2.11% | 0.51% | 0.70% | 2.2% |

Particle Size Analysis

The particle size is tested by the Mastersizer 3000 laser particle size analyzer from Malvern Instrument of the UK. The test uses water as the medium, and a certain amount of the product is placed in the medium, mechanically stirred to fully disperse it in the medium, and determined by the laser particle size analyzer to give out the average particle size.

Determination of the Color of Prolamin Products

The 150-mesh prolamin samples prepared by the methods of Examples 17-22 and Comparative Example and a commercially available prolamin sample (the protein (dry-basis) content 89%, purchased from Zhuhai Rongning Trading Co., Ltd.) are taken. The L (luminance value), a (redness value) and b (yellowness value) of the powder surface color are recorded on a color difference meter (CR2400, Konica Minolta Color Difference Meter, Japan).

As can be seen from Table 3 below, the yellowness value (b) of the prolamin products of Examples 17-22 is significantly reduced compared to the prolamin samples prepared by the commercially available and Comparative Example methods, with a minimum reduction of about 20% and a maximum reduction of about 78%, which indicates that the technique of the present invention also has a good decolorization effect. The products of the present invention have a lower effect on the color of the original application system (such as food or medicine) as an adjuvant.

TABLE 3

LAB color measurement results

| Color Difference Value | Example 17 | Example 18 | Example 19 | Example 20 | Example 21 | Example 22 | Comp. Example | Commercially Available Zein |
|---|---|---|---|---|---|---|---|---|
| L | 93 | 95 | 89 | 86 | 94 | 91 | 80 | 81 |
| a | 2 | 1 | 6 | 10 | 2 | 4 | 17 | 16 |
| b | 21 | 17 | 44 | 60 | 23 | 37 | 77 | 76 |

Odor Evaluation of prolamin

The prolamin samples prepared by the methods of Examples 17-22 and Comparative Example and a commercially available prolamin sample (the protein (dry-basis) content 89%, purchased from Zhuhai Rongning Trading Co., Ltd.) are taken 25 g each. The prolamin samples are held at the room temperature of 20-22° C. and held at the relative humidity of 55%-65% or so. The samples are subjected to zein characteristic odor evaluation under the irradiation of a yellow light source. The odor intensity is divided into 7 grades, which are 1-no, 2-basically no, 3-not obvious, 4-general, 5-a little obvious, 6-obvious, and 7-very obvious. The number of testers is 25. The results are rounded to the average.

As seen in Table 4 below, the characteristic odors of the prolamin products of Example 17-22 are between general (4) and basically no (2), and the technique has a deodorization effect. The products of the present invention have a lower effect on the odor of the original application system (such as food or medicine) as an adjuvant.

Wherein: TS is tensile strength, MPa; F is maximum tensile force (N); δ is film thickness (mm), mm; and W is the width of the film sample (W=15 mm).

Figure 5:
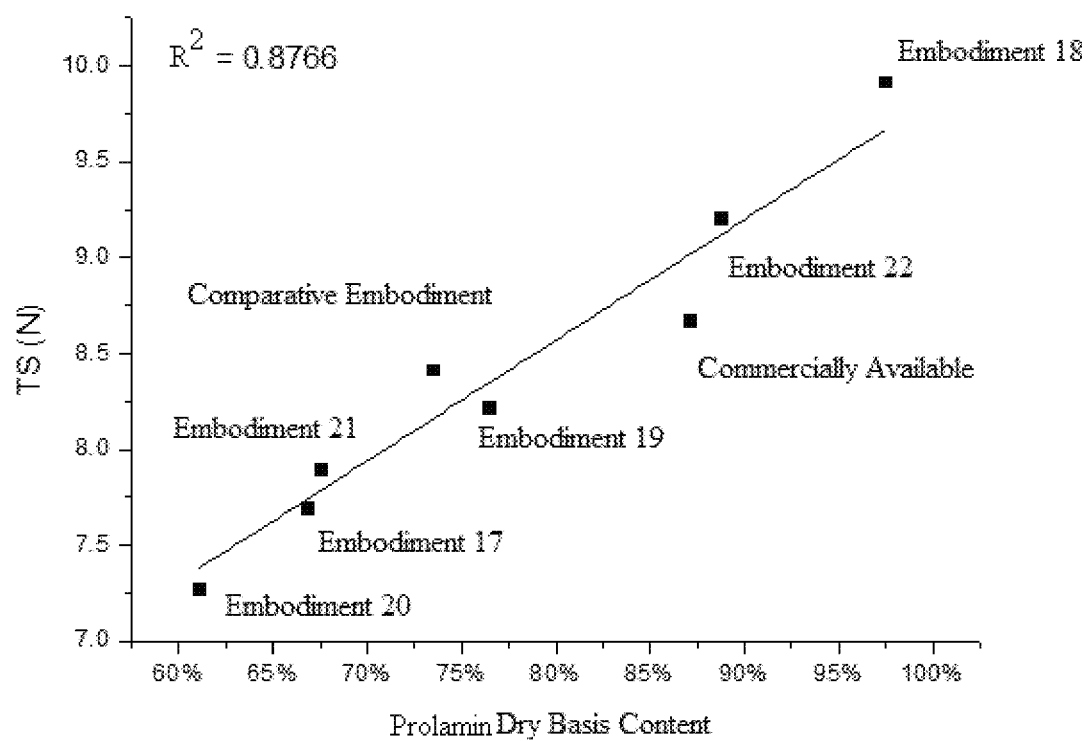
FIG. 5 is a chart showing the tensile stress of films prepared by the zeins obtained in Examples 1-6 and Comparative Example.

As can be seen from FIG. 5, the prolamin products of Examples 17-22 also all have direct film forming properties as compared to the commercially available sample. The tensile strength of the protein film is linear with the content of prolamin in the sample with good fit ($R^2$=0.8766). At the same prolamin content, the tensile strength of the protein film of the sample of the present invention (as in Example 22) is also slightly better than that of the film prepared from the reference commercially available zein.

Comparison of Stability of Prolamin Microspheres

In order to compare the microcapsule stability of the prolamin contained in the samples of Examples 17-22, one

TABLE 4

| | Odor evaluation results | | | | | | |
|---|---|---|---|---|---|---|---|
| | Example 17 | Example 18 | Example 19 | Example 20 | Example 21 | Example 22 | Comp. Example | Commercially Available Zein |
| Commercially Available Zein | 2 | 2 | 3 | 4 | 3 | 3 | 7 | 6 |

Comparison of Film Forming Properties of Prolamin Products

The samples in Examples 17-22, the prolamin sample prepared by the Comparative Example method and the commercially available prolamin sample are subjected to comparative tests. A certain amount of the prolamin sample is weighed and added with a 75% ethanol solution to prepare a 10 wt % protein solution, the protein solution is stirred and mixed uniformly, filtered by a filter paper or filter membrane, respectively added with 20% glycerol and polyethyleneglycol-400 (mass percentage in protein), stirred for 20 min, put into a 80° C. thermostatic water bath, heated and stirred for 15 min, and taken out, a certain volume of the protein film forming solution is injected into a film forming tray and dried by 50° C. air heating to form a film, and after 2 h, the film is peeled and subjected to mechanical property determination after balancing in a 45% relative humidity and room temperature environment for 24 h. The zein film with uniform texture is cut into a size of 15 mm×50 mm, and the thickness is determined according to the method of GB/T6672-2001. Five points are symmetrically selected on the protein film sample, and the thickness is measured and averaged. The mechanical properties of the film are determined by a texture analyzer (TA-XT2i, Stable Micro Systems, UK). During the determination, the tensile speed is 1 mm/s, and the effective determination length of the film is 80 mm. The tensile strength (TS) is the force per unit cross section when the film breaks during stretching. The calculation formula is as follows:

$$TS = \frac{F}{\delta \times W}$$

of the example samples other than Example 18 (such as Example 17) and the Comparative Example sample are extracted with an 80% ethanol solution at 65° C. for 30 min to obtain a sample with the prolamin (dry-basis) content of greater than 85%. Right amounts of the sample of Example 2, the commercially available sample (protein (dry-basis) content of 89%, purchased from Zhuhai Rongning Trading Co., Ltd.), and the newly prepared samples of Example 17, Examples 19-22 and Comparative Example are respectively dissolved in an 80 vol % ethanol solution to prepare a prolamin ethanol solution of which the mass percentage is controlled at 3% The above zein ethanol solution is injected into a proper amount of high-purity water at a high-speed stirring rate of 12000 rpm, and the prolamin microsphere solution is obtained by controlling the mass percentage of the prolamin in the final system to be 1% by membrane separation. The mass percentage of the prolamin in the solution is about 3% after reduced-pressure low-temperature evaporation. The microsphere solution is placed in a graduated container and stored under refrigerated conditions (4° C.), and a significant settling time (i.e., the precipitated layer volume is greater than 5% of the total solution volume) is recorded during storage.

As can be seen from the Table 5 below, the microsphere solution prepared from the prolamin product of the present invention (Example 18) or the secondary prolamin product (Example 17) re-extracted from the product has good stability. The prolamin product of the present invention has a longer stability time than the prolamin products (such as Comparative Example and the commercially available product) prepared by the existing solvent extraction techniques (i.e., extraction directly from the raw material by using ethanol or other organic solvents).

TABLE 5

| | Example 17 | Example 18 | Comp. Example | Commercially Available Zein |
|---|---|---|---|---|
| Microsphere stability | | | | |
| Coagulation Time (days) | 112 | 105 | 90 | 92 |

In view of the exemplary methods and equipment, a method that can be implemented in accordance with the subject matter of the present disclosure will be better understood with reference to the flow diagrams of the drawings. However, for the purpose of simplified explanation, the method is shown and described in a series of block diagrams. It should be understood that some block diagrams may occur in a different order than depicted and described and/or concurrent with other block diagrams, the claimed subject is not limited by the order of the block diagrams. Moreover, not all illustrated block diagrams are required in the implementation method.

What is claimed is:

1. A method for increasing the content of α-prolamin from a raw material, the raw material selected from the group consisting of corn gluten meal, corn endosperm fermented mash, and distiller's grains and comprising α-prolamins, β-prolamin, γ-prolamin and non-prolamin, the method comprising:
   milling and slurrying the raw material;
   treating the raw material with protease to completely hydrolyze or partially hydrolyze at least a part of the β-prolamin, the γ-prolamin and the non-prolamin in the raw material and adding a reagent composition, where the protease is one or more selected from the group consisting of *Aspergillus oryzae* carboxyl endoprotease, *Bacillus subtilis* serine endoprotease, *Bacillus subtilis* metalloendoprotease, bromelain, and papain, and the reagent composition comprises one or more selected from the group consisting of the following substances: tris(2-carboxyethyl)phosphine, a compound having a free thiol group, a compound having a sulfite group, a metal ion and a metal chelator, wherein the treating is at a pH of 3.5-10.5, a temperature of 20° C-65° C., and for 0.2-10 hours;
   performing first filtration by using a difference in particle size to remove the hydrolysate, thereby obtaining a crude product in which the α-prolamins are enriched, where the first filtration is performed by using a filtration pore size of 1 μm -80 pm or a membrane filtration pore size of 10 nm-10 μm; and
   washing, dewatering and drying the crude product to obtain a final product,
   wherein the method does not use organic solvents, the final product comprises prolamins and carbohydrates, where the prolamin accounts for 70 wt % or above of the protein (dry-basis), the α-prolamin accounts for 75 wt % or above of the prolamin, the β-prolamin accounts for 20 wt % or below of the prolamin, and the γ-prolamin accounts for 6 wt % or below of the prolamin.

2. The method according to claim 1, wherein the first filtration is performed by using a filtration pore size of 10 μm-50 μm, or a membrane filtration pore size of 20 nm-1 μm.

3. The method according to claim 1, wherein the raw material comprises the macromolecular carbohydrates and during, before or after the step (2), treatment by hydrolase is used to completely hydrolyze or partially hydrolyze at least a part of macromolecular carbohydrates in the raw material, and performing second filtration by using the difference in particle size to remove the hydrolysate.

4. The method according to claim 3, wherein during the treatment by hydrolase, a hydrolase reagent composition is added to adjust the enzyme, the hydrolase reagent composition comprising one or more selected from the group consisting of the following substances: a metal ion and a metal chelator;
   and/or, the conditions for treatment by hydrolase are selected from: pH 5.0, 63° C.; pH 5.5, 50° C.; pH 3.0, 35° C.; pH 6.5, 45° C.; pH 4.0, 40° C.; pH 6.5, 45° C.; pH 4.5, 60° C.; pH 8, 45° C.; pH 5, 55° C.; pH 7.5, 50° C.; pH 3.5, 30° C.; and pH 5.6, 50° C.

5. The method according to claim 4, wherein the metal ion is one or more selected from the group consisting of alkali metal ion, alkaline earth metal ion and divalent transition metal ion;
   or, the metal chelator is EDTA and/or EGTA.

6. The method according to claim 4, wherein the metal ion is one or more selected from the group consisting of sodium ion, potassium ion, magnesium ion, calcium ion, manganese ion, cobalt ion and zinc ion.

7. The method according to claim 3, wherein the hydrolase is one or more selected from the group consisting of α-amylase, saccharifying enzyme, cellulase, β-glucanase, pullulanase, xylanase, pectinase, arabanase and hemicellulase
   and/or, the treatment by hydrolase is performed under the following conditions: pH 3-8; treatment temperature 30° C. -72° C.; treatment time 0.5 h-12 h.

8. The method according to claim 1, wherein the sulfur-containing compound is one or more selected from the group consisting of mercaptoethanol, dithiothreitol, cysteine and oligopeptide comprising cysteine (peptide consisting of 2-10 amino acids), sulfite, sulfurous acid, bisulfite and pyrosulfite;
   or, the metal ion is one or more selected from the group consisting of alkali metal ion, alkaline earth metal ion and divalent transition metal ion.

9. The method according to claim 1, wherein the metal ion is one or more selected from the group consisting of sodium ion, potassium ion, magnesium ion, calcium ion, manganese ion, cobalt ion and zinc ion;
   or, the metal chelator is EDTA and/or EGTA.

10. The method according to claim 1, wherein the pH of 3.5-10.5 is 3.8-10, the temperature of 20° C.-65° C. is 35° C. -55° C. , and the 0.2-10 hours is 0.5-5 hours.

11. The method according to claim 1, wherein the pH and the temperature are selected from: pH 4.8, 45° C.; pH 7.5, 52° C.; pH 3.8, 35° C.; pH 8.3, 52° C.; pH 8.5, 65° C.; pH 6.5, 45° C.; pH 8.0, 45° C.; pH 10.2, 45° C.; pH 4.2, 35° C.; pH 6.5, 45° C.; pH 4.8, 55° C.; pH 4.8, 53° C.; pH 7.2, 53° C.; pH 7.5, 25° C.; and pH 10.1, 55° C.

12. The method of claim 1, wherein the raw material further comprises one or both of macromolecular carbohydrates and fat.

13. A method for increasing the content of a-prolamin from a raw material, the raw material comprising α-prolamins, β-prolamin, γ-prolamin and non-prolamin the method comprising:
   milling and slurrying the raw material;
   treating the raw material with protease to completely hydrolyze or partially hydrolyze at least a part of the β-prolamin, the γ-prolamin and the non-prolamin in the raw material and adding a reagent composition, where the protease is one or more selected from the group consisting of *Aspergillus oryzae* carboxyl endoprotease, *Bacillus subtilis* serine endoprotease, bromelain, and papain, and the reagent composition comprises one or more selected from the group consisting of the following substances: tris(2-carboxvethyl)phosphine, a compound having a free thiol group, a compound having a sulfite group, a metal ion and a metal chelator, wherein the treating is at a pH of 3.5-10.5, a temperature of 20° C.-65° C., and for 0.2-10 hours;

performing first filtration by using a difference in particle size to remove the hydrolysate, thereby obtaining a crude product in which the α-prolamins are enriched where the first filtration is performed by using a filtration pore size of 1 μm-80 μm or a membrane filtration pore size of 10 nm-10 μm; and (3) washing, dewatering and drying the crude product to obtain a final product, wherein the method does not use organic solvents, the final product comprises prolamins and carbohydrates, where the prolamin accounts for 70 wt % or above of the protein (dry-basis), the α-prolamin accounts for 75 wt % or above of the prolamin, the β-prolamin accounts for 20 wt % or below of the prolamin, and the γ-prolamin accounts for 6 wt % or below of the prolamin.

14. The method of claim 13, wherein the raw material is one or more selected from the group consisting of corn gluten meal, corn endosperm fermented mash, and distiller's grains.

15. The method of claim 13, wherein the raw material further comprises one or both of macromolecular carbohydrates and fat.

* * * * *